United States Patent
Shin et al.

(10) Patent No.: US 11,717,160 B2
(45) Date of Patent: Aug. 8, 2023

(54) METHOD AND PHOTOGRAPHING DEVICE FOR ACQUIRING SIDE IMAGE FOR OCULAR PROPTOSIS DEGREE ANALYSIS, AND RECORDING MEDIUM THEREFOR

(71) Applicant: THYROSCOPE INC., Ulsan (KR)

(72) Inventors: Kyubo Shin, Ulsan (KR); Jaemin Park, Busan (KR); Jongchan Kim, Ulsan (KR); Yoon Won Tak, Ulsan (KR); Hwi Yeon Kim, Ulsan (KR); Eun Yeong Sim, Busan (KR)

(73) Assignee: THYROSCOPE INC., Ulsan (KR)

( * ) Notice: Subject to any disclaimer, the term of this patent is extended or adjusted under 35 U.S.C. 154(b) by 0 days.

(21) Appl. No.: 17/951,681

(22) Filed: Sep. 23, 2022

(65) Prior Publication Data

US 2023/0012806 A1  Jan. 19, 2023

Related U.S. Application Data

(63) Continuation of application No. PCT/KR2022/009259, filed on Jun. 28, 2022.

(30) Foreign Application Priority Data

Jun. 30, 2021 (KR) .......................... 10-2021-0085542
Jun. 28, 2022 (KR) .......................... 10-2022-0078867

(51) Int. Cl.
*A61B 3/14* (2006.01)
*G06T 7/00* (2017.01)
(Continued)

(52) U.S. Cl.
CPC .............. *A61B 3/14* (2013.01); *A61B 5/0077* (2013.01); *A61B 5/1079* (2013.01);
(Continued)

(58) Field of Classification Search
CPC ....... A61B 3/14; A61B 5/0077; A61B 5/1079; A61B 5/4227; A61B 5/7275;
(Continued)

(56) References Cited

U.S. PATENT DOCUMENTS

| | | | | |
|---|---|---|---|---|
| 2010/0289922 | A1* | 11/2010 | Brenner | ............... H04N 23/698 348/E9.002 |
| 2014/0313359 | A1* | 10/2014 | Hwang | ............... H04N 23/698 348/218.1 |

(Continued)

FOREIGN PATENT DOCUMENTS

| | | |
|---|---|---|
| CN | 109543728 A | 3/2019 |
| CN | 110246158 A | 9/2019 |

(Continued)

OTHER PUBLICATIONS

Notice of Allowance of KR 10-2022-0079770 dated Oct. 31, 2022.
(Continued)

*Primary Examiner* — Mohammed A Hasan
(74) *Attorney, Agent, or Firm* — Dinsmore & Shohl LLP; Yongsok Choi, Esq.

(57) ABSTRACT

The present application relates to a method of acquiring a side image for analyzing the degree of ocular proptosis. According to an embodiment, an image acquisition method is provided which is including: acquiring a front image of the subject's face while guidance is given to satisfy a first photographing condition; generating panorama guidance on the basis of position information of a first point and a second point extracted from the front image; providing guidance on movement of a photographing device to acquire a preview image corresponding to the panorama guidance; and acquiring a side image of the subject's face while guidance is given to satisfy a second photographing condition. The first captured image shows iris areas of the subject, and the second (Continued)

captured image shows an outer canthus and a cornea of one of the subject's eyes.

17 Claims, 21 Drawing Sheets

(51) Int. Cl.
  *A61B 5/00* (2006.01)
  *A61B 5/107* (2006.01)
  *G06T 7/62* (2017.01)
  *H04N 23/60* (2023.01)
  *H04N 23/611* (2023.01)
  *H04N 23/63* (2023.01)
  *H04N 23/698* (2023.01)

(52) U.S. Cl.
  CPC .......... *A61B 5/4227* (2013.01); *A61B 5/7275* (2013.01); *G06T 7/0012* (2013.01); *G06T 7/62* (2017.01); *H04N 23/611* (2023.01); *H04N 23/633* (2023.01); *H04N 23/64* (2023.01); *H04N 23/698* (2023.01); *G06T 2207/30041* (2013.01)

(58) Field of Classification Search
  CPC ..... A61B 5/1077; A61B 5/1072; A61B 3/107; G06T 7/0012; G06T 7/62; G06T 2207/30041; H04N 23/611; H04N 23/633; H04N 23/64; H04N 23/698
  USPC ........................................................ 351/206
  See application file for complete search history.

(56) References Cited

U.S. PATENT DOCUMENTS

| | | | |
|---|---|---|---|
| 2019/0274542 A1* | 9/2019 | Imamura | A61B 3/102 |
| 2019/0370959 A1 | 12/2019 | Krishna et al. | |
| 2020/0066394 A1* | 2/2020 | Toyoda | G16H 10/60 |
| 2020/0297206 A1 | 9/2020 | Zakharov et al. | |

FOREIGN PATENT DOCUMENTS

| | | | |
|---|---|---|---|
| CN | 111839455 | A | 10/2020 |
| JP | 2016032587 | A | 3/2016 |
| JP | 2017503276 | A | 1/2017 |
| JP | 2018099174 | A | 6/2018 |
| KR | 1020080105723 | A | 12/2008 |
| KR | 1020140089132 | A | 7/2014 |
| KR | 1020140105313 | A | 9/2014 |
| KR | 1020140108417 | A | 9/2014 |
| KR | 1020150107565 | A | 9/2015 |
| KR | 1020190082149 | A | 7/2019 |
| KR | 102047237 | B1 | 12/2019 |
| KR | 102058883 | B1 | 12/2019 |
| KR | 1020200005060 | A | 1/2020 |
| KR | 1020200077461 | A | 6/2020 |
| KR | 1020200108993 | A | 9/2020 |
| KR | 1020200133923 | A | 12/2020 |
| KR | 1020210004695 | A | 1/2021 |
| KR | 102223478 | B1 | 3/2021 |
| KR | 1020210026597 | A | 3/2021 |
| KR | 102347551 | B1 | 1/2022 |
| KR | 102379061 | B1 | 4/2022 |
| WO | 2020023959 | A1 | 1/2020 |

OTHER PUBLICATIONS

International Search Report and Written Opinion of PCT/KR2022/009452 dated Oct. 13, 2022.
International Search Report and Written Opinion of PCT/KR2022/009259 dated Oct. 6, 2022.
International Search Report and Written Opinion of PCT/KR2022/009356 dated Oct. 6, 2022.
Office Action of KR 10-2022-0080423 dated Sep. 20, 2022.
Notice of Allowance of KR 10-2021-0085542 dated Dec. 22, 2021.
Office Action of KR 10-2021-0085542 dated Aug. 20, 2021.

* cited by examiner

Acquisition of user responses
- Conjunctival hyperemia
- Eyelid redness
- Conjunctival edema
- Lacrimal edema
- Eyelid edema
- Spontaneous retrobulbar pain
- Pain on attempted upward or downward gaze CAS evaluation items(Advanced)
- Degree of protrusion
- Visual acuity
- Eyeball movement (a)   (b)

METHOD AND PHOTOGRAPHING DEVICE FOR ACQUIRING SIDE IMAGE FOR OCULAR PROPTOSIS DEGREE ANALYSIS, AND RECORDING MEDIUM THEREFOR

CROSS-REFERENCE TO RELATED APPLICATIONS

This application is a continuation of International Application No. PCT/KR2022/009529 filed on Jun. 28, 2022, which claims priority to Korean Patent Application No. 10-2021-0085542 filed on Jun. 30, 2021 and Korean Patent Application No. 10-2022-0078867 filed on Jun. 28, 2022, the entire contents of which are herein incorporated by reference.

TECHNICAL FIELD

The present disclosure relates to a method of acquiring a side image for ocular proptosis degree analysis, a photographing device for performing the method, and a recording medium therefor.

BACKGROUND ART

With the development of artificial intelligence technology, a technology for analyzing a diagnostic image acquired by photographing a user to acquire information on the health status of the user, and for providing, on the basis of the information, guidance on visiting a hospital in order for the user to visit the hospital in an early stage of a disease has been actively developed.

For example, Thyroscope Inc., the applicant, is a company that provides solutions to manage the thyroid. After developing a software medical device for predicting a risk of thyroid dysfunction to provide guidance on visiting a hospital, the applicant developed an artificial intelligence model for predicting thyroid eye disease by using learning of digital images of faces, and is about to release a software medical device for predicting a risk of thyroid eye disease to provide guidance on visiting a hospital.

As a consumer survey on the software medical device for predicting thyroid eye disease was conducted, it was found that the software medical device can be used for patients who want to check the time of a hospital visit and can be used to observe a treatment progress in a clinical process for a medication for thyroid eye disease. Thus, in order to observe a treatment progress of thyroid eye disease and record a result of observation as data, there is a demand for the development of a precise photographing technique for acquiring a side image appropriate to analyze the degree of ocular proptosis.

SUMMARY

Technical Problem

The disclosure in the present application is directed to providing a method of acquiring a side image of a face, a photographing device for performing the method, and a recording medium therefor, so that the degree of ocular proptosis is monitored without a hospital visit.

In addition, the disclosure in the present application is directed to providing a method of acquiring an image, a photographing device for performing the method, and a recording medium therefor, the method being capable of acquiring a facial image appropriate to be used as a diagnostic image even when it is difficult to detect an up-down rotation angle of a face accurately.

In addition, the disclosure in the present application is directed to providing a method and a system for monitoring a clinical activity score for thyroid eye disease, so that thyroid eye disease is found early for ordinary people or patients being treated for thyroid dysfunction.

Technical problems to be solved by the present application are not limited to the aforementioned technical problems, and other technical problems which are not mentioned will be clearly understood by those skilled in the art from the present application.

Technical Solution

According to an aspect of the present application, disclosed is a method of acquiring a facial image of a subject to analyze the degree of ocular proptosis. The method may include: acquiring a front image of the subject's face while guidance is given to satisfy a first photographing condition, wherein satisfying the first photographing condition at least includes a condition in which the subject's both eyes are placed at predetermined areas in a first captured image; generating panorama guidance on the basis of position information of a first point and a second point extracted from the front image, wherein the panorama guidance is generated in a horizontal direction with respect to a front of the face, and the first point and the second point are spaced apart from each other in a vertical direction with respect to the front of the face; providing guidance on movement of a photographing device to acquire a preview image corresponding to the panorama guidance, wherein monitoring is performed such that a vertical separation distance between the first point and the second point extracted from the preview image and an initial separation distance have a difference within a predetermined error range; and acquiring a side image of the subject's face while guidance is given to satisfy a second photographing condition, wherein the second photographing condition is a condition in which a vertical separation distance between the first point and the second point extracted from the second captured image and the initial separation distance have a difference within the predetermined error range. Herein, in order for the acquired images to be used in calculating the degree of ocular proptosis, the first captured image shows iris areas of the subject and the second captured image shows an outer canthus and a cornea of one of the subject's eyes.

According to another aspect of the present application, disclosed is a non-transitory computer-readable medium for storing one or more instructions therein. The non-transitory computer-readable medium may enable, when executed by one or more processors of a computing device, the computing device to perform the above-described method.

According to still another aspect of the present application, disclosed is a photographing device for acquiring a facial image of a subject to analyze the degree of ocular proptosis. The device may include a communication part, a storage part configured to store one or more instructions therein, and a controller configured to execute the one or more instructions stored in the storage part. The controller may be configured to, by executing the one or more instructions, acquire a front image of the subject's face while guidance is given to satisfy a first photographing condition, generate panorama guidance on the basis of position information of a first point and a second point extracted from the front image, provide guidance on movement of the photographing device to acquire a preview image corresponding to the panorama guidance, and acquire a side image of the subject's face while guidance is given to satisfy a second photographing condition, wherein the first photographing condition at least includes a condition in which the subject's both eyes are placed at determined areas in a first captured image, the panorama guidance is generated in a horizontal direction with respect to a front of the face, and the first point and the second point are spaced apart from each other in a vertical direction with respect to the front of the face, and the second photographing condition is at least a condition in which a vertical separation distance between the first point and the second point extracted from the second captured image and an initial separation distance have a difference within a predetermined error range.

However, the solving means of the problems of the present disclosure are not limited to the above-described solving means and solving means which have not been mentioned may be clearly understood from the specification by those skilled in the art.

Advantageous Effects

According to the disclosure in the present application, a face side image appropriate to monitor a change in the degree of ocular proptosis can be acquired using digital cameras, such as smartphones, which ordinary people can use.

The effect of the present application is not limited to the above-mentioned effect, other effects which are not mentioned will be clearly understood by those skilled in the art from the present application.

DETAILED DESCRIPTION

Figure 1:
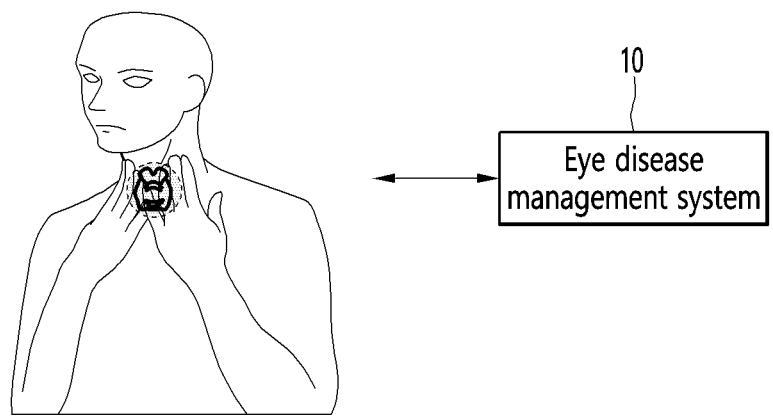
FIG. 1 is a diagram illustrating an eye disease management system according to an embodiment.

The above-described objectives, features, and advantages of the present application will be more apparent from the following detailed description with reference to the accompanying drawings. In addition, various modifications may be made to the present application, and various embodiments of the present application may be practiced. Therefore, specific embodiments will be described in detail below with reference to the accompanying drawings.

Throughout the specification, the same reference numerals denote the same elements in principle. In addition, elements having the same function within the same scope illustrated in the drawings of the embodiments are described using the same reference numerals, and a redundant description will be omitted.

A detailed description of a well-known function or configuration relating to the present application is omitted when determined as obfuscating the nature and gist of the present application. In addition, throughout the present specification, the terms first, second, and so on are used only to distinguish from one element to another.

In addition, the terms "module" and "part" that are used to name an element in the description below are used considering only the ease with which the present specification is written. The terms are not intended as having different special meanings or functions and thus may be used individually or interchangeably.

In the following embodiments, an expression used in the singular encompasses the expression of the plural, unless it has a clearly different meaning in the context.

In the following embodiments, it is to be understood that terms such as "including", "having", etc. are intended to indicate the existence of features or elements disclosed in the specification, and are not intended to preclude the possibility that one or more other features or elements may be added.

Sizes of elements in the drawings may be exaggerated or reduced for convenience of description. For example, any size and thickness of each element shown in the drawings are shown for convenience of description, and the present disclosure is not limited thereto.

In a case in which a particular embodiment is realized otherwise, a particular process may be performed out of the order described. For example, two processes described in succession may be performed substantially simultaneously, or may proceed in the order opposite to the order described.

In the following embodiments, when elements are referred to as being connected to each other, the elements are directly connected to each other or the elements are indirectly connected to each other with intervening elements therebetween. For example, in the present specification, when elements are referred to as being electrically connected to each other, the elements are directly electrically connected to each other or the elements are indirectly electrically connected with intervening elements therebetween.

According to an aspect of the present application, disclosed is a method of acquiring a facial image of a subject to analyze the degree of ocular proptosis. The method may include: acquiring a front image of the subject's face while guidance is given to satisfy a first photographing condition, wherein satisfying the first photographing condition at least includes a condition in which the subject's both eyes are placed at predetermined areas in a first captured image; generating panorama guidance on the basis of position information of a first point and a second point extracted from the front image, wherein the panorama guidance is generated in a horizontal direction with respect to a front of the face, and the first point and the second point are spaced apart from each other in a vertical direction with respect to the front of the face; providing guidance on movement of a photographing device to acquire a preview image corresponding to the panorama guidance, wherein monitoring is performed such that a vertical separation distance between the first point and the second point extracted from the preview image and an initial separation distance have a difference within a predetermined error range; and acquiring a side image of the subject's face while guidance is given to satisfy a second photographing condition, wherein the second photographing condition is a condition in which a vertical separation distance between the first point and the second point extracted from the second captured image and the initial separation distance have a difference within the predetermined error range. Herein, in order for the acquired images to be used in calculating the degree of ocular proptosis, the first captured image shows iris areas of the subject and the second captured image shows an outer canthus and a cornea of one of the subject's eyes.

In several embodiments, satisfying the first photographing condition may at least includes a condition in which a left-right rotation angle of the subject's face does not exceed a predetermined first reference value.

In several embodiments, satisfying the first photographing condition may at least includes a condition in which a level of smiling of the subject based on facial expression information of the subject does not exceed a predetermined second reference value.

In several embodiments, satisfying the first photographing condition may at least includes a condition in which an up-down rotation angle of the subject's face does not exceed a predetermined third reference value.

In several embodiments, satisfying the first photographing condition may at least includes a condition in which ambient brightness does not exceed a fourth reference value.

In several embodiments, satisfying the second photographing condition may at least includes a condition in which the subject's ear is placed at a predetermined area in the second captured image.

In several embodiments, the first point may be a point at a tip of the nose, and the second point may be a point at a tip of the chin in an outline of the face.

In several embodiments, the providing the guidance on the movement of the photographing device to acquire the preview image corresponding to the panorama guidance may include: acquiring the preview image according to a predetermined frame rate; determining whether the vertical separation distance between the first point and the second point extracted from the acquired preview image and the initial separation distance have a difference within the predetermined error range; and outputting a guidance for adjusting a distance between the photographing device and the face when it is determined that the difference is out of the predetermined error range.

In several embodiments, in the method, the outputting the guide for adjusting the distance between the photographing device and the face when it is determined that the difference is out of the predetermined error range may include: outputting the guidance for moving the photographing device away from the face when it is determined that the vertical separation distance between the first point and the second point extracted from the acquired preview image is longer than the initial separation distance to the extent of being out of the predetermined error range; or outputting the guidance for moving the photographing device close to the face when it is determined that the vertical separation distance between the first point and the second point extracted from the acquired preview image is shorter than the initial separation distance to the extent of being out of the predetermined error range.

In several embodiments, the providing the guidance on the movement of the photographing device to acquire the preview image corresponding to the panorama guidance may include: determining whether a position of the first point extracted from the acquired preview image is moved by less than a fifth reference value from a position of the first point extracted from the front image; and outputting a guidance for moving the photographing device upward or downward with respect to the face when it is determined that the position of the first point extracted from the acquired preview image is moved by more than the fifth reference value from the position of the first point extracted from the front image.

In several embodiments, the providing the guidance on the movement of the photographing device to acquire the preview image corresponding to the panorama guidance may include: determining whether a position of the second point extracted from the acquired preview image is moved by less than a sixth reference value from a position of the second point extracted from the front image; and outputting the guidance for moving the photographing device upward or downward with respect to the face when it is determined that the position of the second point extracted from the acquired preview image is moved by more than the sixth reference value from the position of the second point extracted from the front image.

In several embodiments, in the providing the guidance on the movement of the photographing device to acquire the preview image corresponding to the panorama guidance, at least part of the preview image may be acquired as a third captured image, and the first captured image, the second captured image, and the third captured image may be edited into and stored as a panoramic image.

In several embodiments, video images may be stored by continuously acquiring images from a time point when the first captured image is acquired to a time point when the second captured image is acquired.

In several embodiments, satisfying the second photographing condition may at least includes a condition in which one of the subject's eyes is not detected in the second captured image.

In several embodiments, the method may include: acquiring a diameter value of the iris areas detected in the first captured image; acquiring a distance value between the outer canthus detected in the second captured image and the cornea furthest from the outer canthus; and acquiring a ratio between the distance value and the diameter value, and acquiring the degree of ocular proptosis by predicting the distance value by applying a characteristic value of the iris areas to the ratio.

According to another aspect of the present application, disclosed is a non-transitory computer-readable medium in which one or more instructions are stored. The non-transitory computer-readable medium may enable, when executed by one or more processors of a computing device, the computing device to perform the above-described method.

According to still another aspect of the present application, disclosed is a photographing device for acquiring a facial image of a subject to analyze the degree of ocular proptosis. The device may include a communication part, a storage part configured to store one or more instructions therein, and a controller configured to execute the one or more instructions stored in the storage part. The controller may be configured to, by executing the one or more instructions, acquire a front image of the subject's face while guidance is given to satisfy a first photographing condition generate panorama guidance on the basis of position information of a first point and a second point extracted from the front image, provide guidance on movement of the photographing device to acquire a preview image corresponding to the panorama guidance, and acquire a side image of the subject's face while guidance is given to satisfy a second photographing condition, wherein the first photographing condition at least includes a condition in which the subject's both eyes are placed at predetermined areas in a first captured image, the panorama guidance is generated in a horizontal direction with respect to a front of the face, and the first point and the second point are spaced apart from each other in a vertical direction with respect to the front of the face, and the second photographing condition is at least a condition in which a vertical separation distance between the first point and the second point extracted from the second captured image and an initial separation distance have a difference within a predetermined error range.

According to the present application, disclosed are a method of acquiring an image used to manage thyroid eye disease, and a system for managing thyroid eye disease (for example, hospital visit guidance) on the basis of the method.

In the present specification, the term "eye" refers to an area exposed to the outside through the eye shape determined by eyelids with respect to an eyeball. In other words, in the present specification, the term "eye" may be included in an "eyeball" in terms of concept.

In the present specification, the term "iris area" may refer to an area of a combination of the iris of an eyeball and the pupil of the eyeball.

In the present specification, the term "subject" may refer to a target (for example, a person) of which an image is captured by a thyroid eye disease management system.

In the present specification, the term "preview image" may refer to an image acquired according to the frame rate predetermined at the time point of taking an image. Specifically, an image photographing operation according to a user input is started, or an automatic photographing operation is started with a pre-stored condition satisfied. In response thereto, a captured image is stored, wherein an image captured before this storing step may be referred to as a "preview image".

In the present specification, the term "captured image" may refer to a finally acquired image according to an image photographing operation. Specifically, the term "captured image" may refer to an image that is stored in response to the start of an image photographing operation according to a user input or an automatic photographing operation after a pre-stored condition is satisfied.

In the present specification, the term "photographing guidance" may refer to performing a function of assisting in taking an image. For example, the "photographing guidance" may be in the form of a line or letter output together on a preview image being output on a display of a user terminal. As another example, the "photographing guidance" may be in the form of voice output to assist in photographing through a speaker of a user terminal. However, no limitation thereto is imposed.

In the present specification, the term "left-right rotation angle" of a face may refer to an angle (yaw) of rotation on a virtual vertical axis passing through the center of the hair side of the face. Specifically, when a face is facing forward, the left-right rotation angle of the face may be 0°. When a face is facing to the right, the left-right rotation angle of the face may be 90°. When a face is facing to the left, the left-right rotation angle of the face may be −90°.

In the present specification, the term "up-down rotation angle" may refer to an angle (pitch) of rotation on a virtual horizontal axis passing through the centers of the ear sides of the face. Specifically, when a face is facing forward, the up-down rotation angle of the face may be 0°. When a face is facing upward (for example, toward the sky), the up-down rotation angle of the face may be 90°. When a face is facing downward (for example, toward the ground), the up-down rotation angle of the face may be −90°.

In the present specification, the term "eye disease" may refer to thyroid eye disease, which is autoimmune eye disease known to occur in association with thyroid disease. Statistically, thyroid eye disease is mostly accompanied by hyperthyroidism, but may occur before hyperthyroidism occurs or when thyroid function is normal. Accordingly, the "eye disease" described in the present specification should be interpreted as describing a disease to be managed using an eye disease management system, as a disease name commonly called in the health care industry, and should not be interpreted as meaning that the mechanism of development of the disease being monitored is due to thyroid.

1. Eye Disease Management System (1) General System

FIG. 1 is a diagram illustrating an eye disease management system 10 according to an embodiment.

The eye disease management system 10 predicts an eye disease, or checks and manages disease progress after knowing the presence of eye disease.

According to an embodiment, the eye disease management system 10 may acquire an image of a subject and analyze the acquired image to predict the possibility of eye disease. As a specific example, the eye disease management system 10 may acquire a front face image of a subject, may analyze the acquired front face image to predict a clinical activity score (CAS), and may determine whether the predicted clinical activity score exceeds a reference value so as to predict the possibility of occurrence of thyroid eye disease. As another specific example, the eye disease management system 10 may acquire a side face image of a subject, may analyze the acquired side face image to predict the degree of ocular proptosis or monitor a change in the degree of ocular proptosis.

Figure 2:
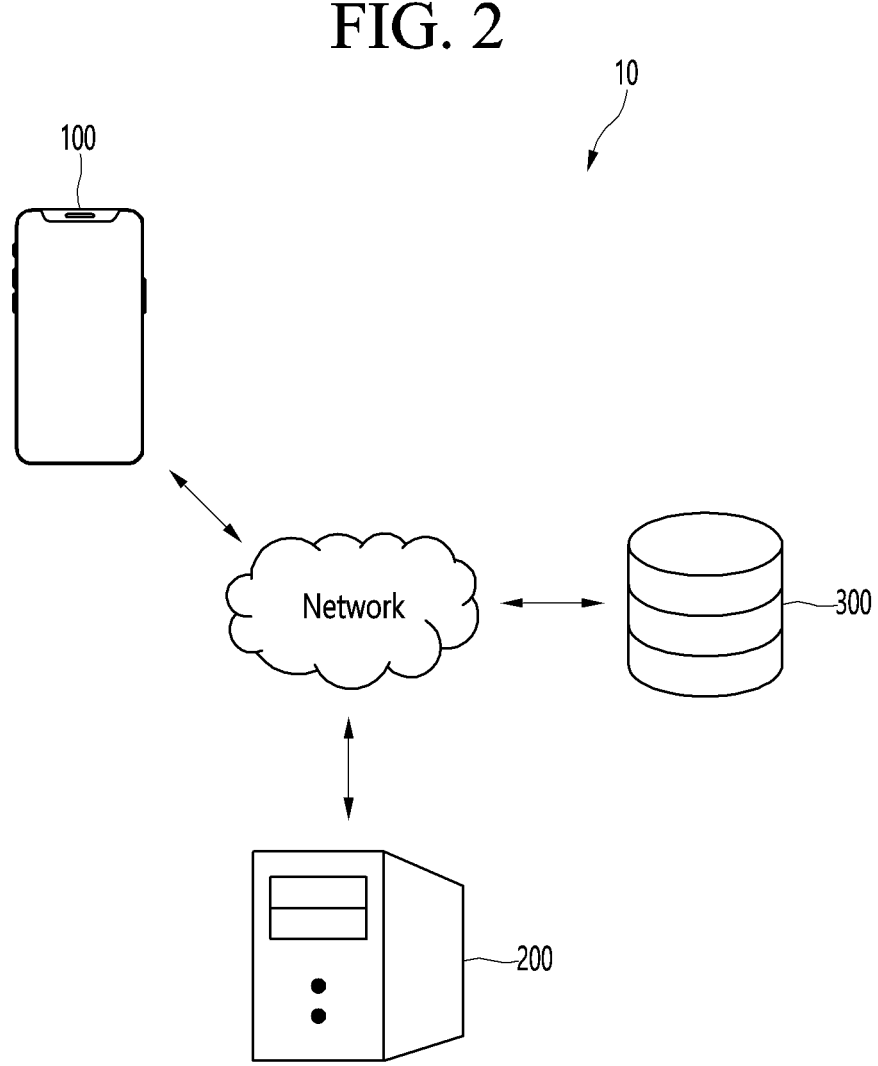
FIG. 2 is a diagram illustrating an eye disease management system including a user terminal.

FIG. 2 is a diagram illustrating an eye disease management system including a user terminal.

In several embodiments, the user terminal 100 may be connected to another user terminal 100 and/or an eye disease management server 200 over a network. In general, the network may be a communication network and/or a wide area network (WAN). In a particular embodiment, the network may be the Internet.

The user terminal 100 may acquire an image of a body part of a subject. The acquired image may be an image captured satisfying a predetermined condition so as to be used by the eye disease management server 200 for diagnosis. The user terminal 100 may transmit the acquired image to the eye disease management server 200.

The eye disease management server 200 may generate information on thyroid eye disease by analyzing an image. For example, the eye disease management server 200 may analyze an image to calculate a clinical activity score, and may evaluate whether the clinical activity score is equal to or greater than a score of 3 so as to provide information for inducing a hospital visit for treating thyroid eye disease at an appropriate time. As another example, the eye disease management server 200 may analyze an image to estimate the degree of ocular proptosis, and may store information on the degree of ocular proptosis to provide a user with information on a change in the degree of ocular proptosis.

The eye disease management system 10 may be constructed with at least some of the elements shown in FIG. 2 omitted, or may be constructed with an element not shown in FIG. 2 additionally included.

(2) Elements of User Terminal

Figure 3:
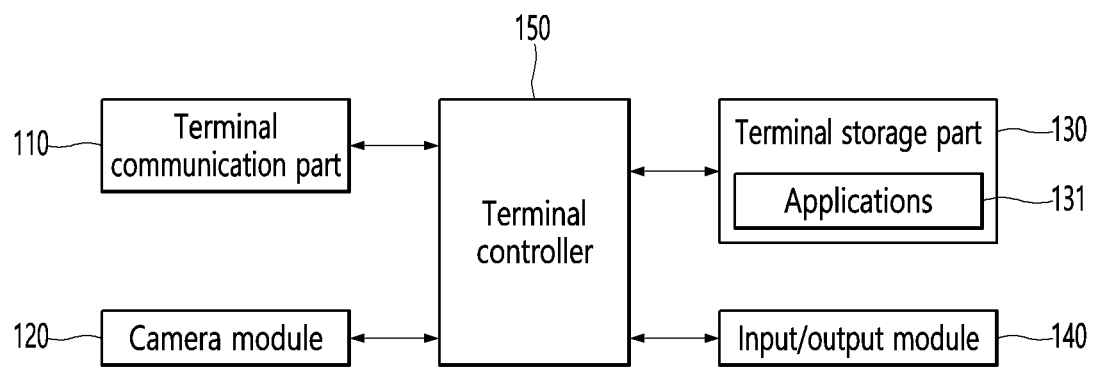
FIG. 3 is a block diagram illustrating a user terminal according to an embodiment.

FIG. 3 is a block diagram illustrating a user terminal according to an embodiment.

According to an embodiment, the user terminal 100 includes a terminal communication part 110, a camera module 120, a terminal storage part 130, an input/output module 140, and a terminal controller 150. For example, the user terminal 100 may be a smartphone, a tablet device, a laptop computer, a personal computer, or a combination thereof, but is not limited thereto.

The terminal communication part 110 may include a wireless communication module and/or a wired communication module. Examples of the terminal communication part 110 a wired/wireless local area network (LAN) module, a WAN module, an Ethernet module, a Bluetooth module, a Zigbee module, a universal serial bus (USB) module, an IEEE 1394 module, a Wi-Fi module, or a combination thereof, but are not limited thereto.

The camera module 120 is a digital camera, and may include an image sensor and an image processor. The image sensor is a device for converting an optical image into electrical signals, and may be provided as a chip in which multiple photodiodes are integrated. Examples of the image sensor may include a charge-coupled device (CCD), a complementary metal-oxide-semiconductor (CMOS), etc. In the meantime, the image processor may perform image processing on captured results, and may generate image information.

The terminal storage part 130 is a memory, and the memory may be a storage means for storing data readable by a microprocessor. Examples of the terminal storage part 130 may include a hard disk drive (HDD), a solid state disk (SSD), a silicon disk drive (SDD), ROM, RAM, etc. In the terminal storage part 130, the following are stored: an operating system (OS) for running the user terminal, various programs (and/or application programs 131) to be run on the user terminal, and various types of data to be referenced by the programs.

The input/output module 140 may include a user input part, an output part, and/or an input/output interface. The user input part receives a user's input to the user terminal 100. The received input may be transmitted to the terminal controller 150. According to an embodiment, the user input part may receive a user's input through a touch display. The output part outputs various types of information according to control commands of the terminal controller 150. According to an embodiment, the output part may include a display for outputting information visually to a user. Alternatively, the output part may include a speaker for outputting information audibly to a user, and a vibration motor for outputting information tactually to a user.

The input/output interface is, for example, an interface for transmitting commands or data input from a user or other external devices to other element(s) of the user terminal 100.

Furthermore, the input/output interface may output commands or data received from other element(s) of the user terminal 100 to a user or other external devices.

The terminal controller 150 may include at least one processor. Herein, each processor may perform a predetermined operation by executing at least one instruction stored in the memory. According to an embodiment, the terminal controller 150 may control the overall operation of the components included in the user terminal 100. In other words, the user terminal 100 may be controlled or operated by the terminal controller 150. The terminal controller 150 may, for example, execute operations or data processing related to control and/or communication of one or more other elements of the user terminal 100.

The terminal controller 150 may include one or more of the following: a central processing unit (CPU), an application processor (AP), and a communication processor (CP).

The user terminal 100 may be provided with at least some of the elements shown in FIG. 3 omitted, or may be provided with an element not shown in FIG. 3 additionally included.

hereinafter, unless otherwise specified, the operation of the user terminal 100 may be interpreted as being performed by the terminal controller 150.

2. Operation of Eye Disease Management System—Image Acquisition Method

Figure 4:
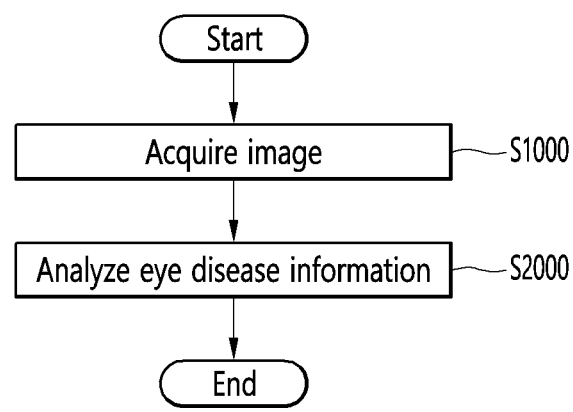
FIG. 4 is a diagram illustrating the operation of an eye disease management system according to an embodiment.

FIG. 4 is a diagram illustrating the operation of an eye disease management system according to an embodiment.

The eye disease management system 10 may acquire an image in step S1000 and may acquire eye disease information in step S2000. An image acquisition method and an image analysis method will be described in detail below.

According to an embodiment, both the image acquisition method and the image analysis method may be performed by a user terminal 100, and herein, the user terminal 100 is the only device constituting the eye disease management system 10.

According to another embodiment, the image acquisition method may be performed by a user terminal 100, and the image analysis method may be performed by an eye disease management server 200. Herein, the eye disease management system 10 may include at least an electronic device 100 and the eye disease management server 200. Herein, the user terminal 100 and the eye disease management server 200 are connected to each other so as to exchange data, so that necessary data is transmitted and received therebetween.

According to still another embodiment, a partial operation of the image acquisition method may be performed by the user terminal 100, and the remaining operation may be performed by the eye disease management server 200. In addition, a partial operation of the image analysis method may be performed by the user terminal 100, and the remaining operation may be performed by the eye disease management server 200.

Hereinafter, a detailed embodiment will be described assuming that the user terminal 100 performs the image acquisition method independently and the eye disease management server 200 performs the image analysis method independently. However, this does not mean that the disclosure described in the present specification is limited to being performed by the subject below, but one embodiment is merely described for convenience of description.

(1) Image Acquisition Method—First Exemplary Embodiment

In a system for predicting thyroid eye disease by analyzing an image, it is necessary to take an appropriate diagnostic image in order to improve the accuracy of prediction of thyroid eye disease. To this end, it is necessary to acquire a diagnostic image while a predetermined photographing condition is satisfied. Accordingly, in the present embodiment, a method of acquiring an image used in analyzing thyroid eye disease will be described in detail.

In an eye disease management system 10 according to an embodiment, an image satisfying a first photographing condition may be acquired.

The first photographing condition is a criterion for image acquisition of the eye disease management system 10, and may be determined by evaluating the following: whether a subject's both eyes are placed at appropriate positions in a diagnostic image; whether an up-down rotation angle of the subject's face is within an appropriate range; whether a left-right rotation angle of the subject's face is within an appropriate range; whether the subject's face makes up an appropriate proportion (portion) of the image; whether the subject's smile level is within an appropriate range; and/or whether ambient brightness is within an appropriate range.

As a specific example, satisfying the first photographing condition may mean that a subject's both eyes are placed at predetermined areas in a first captured image, a left-right rotation angle of the subject's face does not exceed a predetermined first reference value, and the subject's smile level based on facial expression information of the subject does not exceed a predetermined second reference value.

According to another embodiment, satisfying the first photographing condition may mean that a subject's both eyes are placed at predetermined areas in a first captured image, a left-right rotation angle of the subject's face does not exceed a predetermined first reference value, the subject's smile level based on facial expression information of the subject does not exceed a predetermined second reference value, and an up-down rotation angle of the subject's face does not exceed a predetermined third reference value.

According to still another embodiment, satisfying the first photographing condition may mean that a subject's both eyes are placed at predetermined areas in a first captured image, a left-right rotation angle of the subject's face does not exceed a predetermined first reference value, the subject's smile level based on facial expression information of the subject does not exceed a predetermined second reference value, an up-down rotation angle of the subject's face does not exceed a predetermined third reference value, and ambient brightness does not exceed a fourth reference value.

Without being limited thereto, the thyroid eye disease management system 10 may determine whether the first photographing condition is satisfied by analyzing at least some of the above-described several evaluation indicators or by analyzing additional indicators. Hereinafter, an embodiment of the image acquisition method of the present disclosure will be described with reference to FIG. 5.

Figure 5:
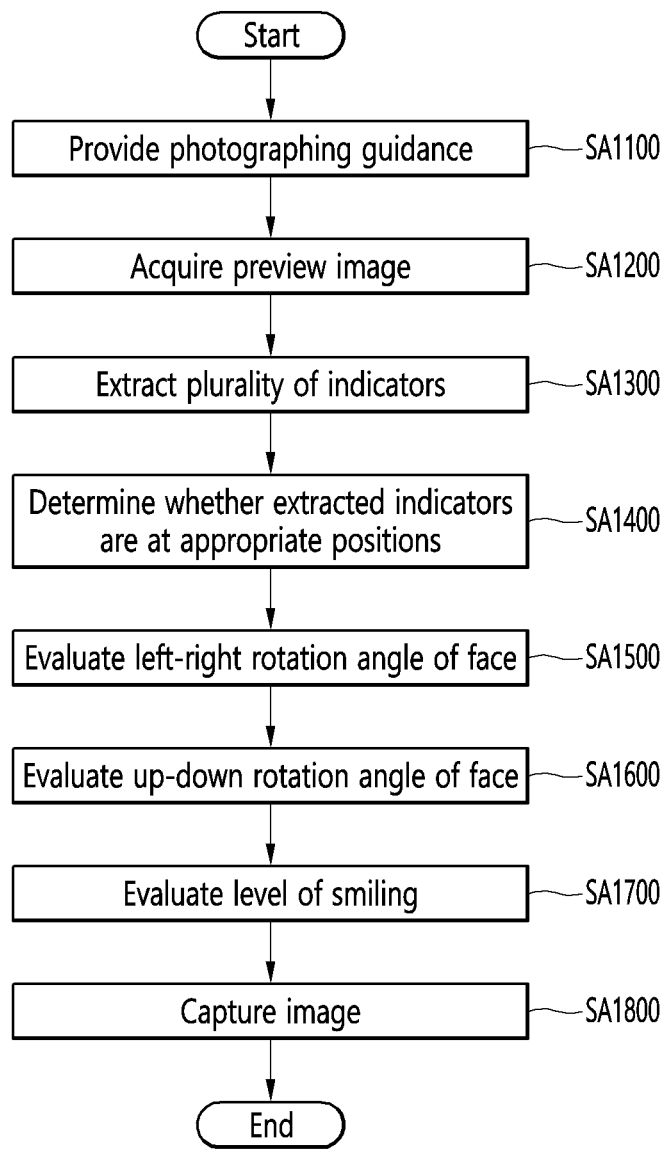
FIG. 5 is a diagram illustrating an image acquisition method according to an embodiment.

FIG. 5 is a diagram illustrating an image acquisition method according to an embodiment.

The user terminal 100 may provide photographing guidance in step SA1100. The terminal controller 150 may provide the user with the photographing guidance through the input/output module 140.

While a preview image is acquired and provided through the input/output module 140, the user terminal 100 may provide the photographing guidance such that the photographing guidance overlap the preview image. In this case, the photographing guidance is provided at fixed positions on the input/output module 140, and the positions at which the photographing guidance is provided do not change according to the characteristics of the acquired preview image.

The photographing guidance may be instructions provided to the user to acquire an image appropriate for the above-described several evaluation indicators. The photographing guidance may be instructions about some of the evaluation indicators that are set to be evaluated according to a photographing condition stored in the user terminal 100. For example, the user terminal 100 may display the points at which a subject's both eyes need to be positioned, but may not provide the photographing guidance corresponding to the remaining indicators. As another example, the user terminal 100 may display the points at which a subject's both eyes need to be positioned and the area in which the subject's face needs to be included, but may not provide the photographing guidance corresponding to the remaining indicators. In the meantime, the photographing guidance may be instructions about all of the evaluation indicators that are set to be evaluated according to the photographing condition stored in the user terminal 100. An embodiment of the photographing guidance of the present disclosure will be described below with reference to FIGS. 6 and 7.

The user terminal 100 may acquire a preview image in step SA1200. The terminal controller 150 may acquire the preview image with the camera module 120 in step SA1200. The terminal controller 150 may acquire the preview image in step SA1200 while the photographing guidance is provided through the input/output module 140. The preview image may be acquired according to a predetermined frame rate.

The user terminal 100 may extract a plurality of indicators from the acquired preview image in step SA1300. The terminal controller 150 may extract the plurality of indicators by using an algorithm stored in the terminal storage part 130 in step SA1300.

The user terminal 100 may perform step SA1300 on at least part of the acquired preview image. This is because the time that it takes to, after a preview image is acquired, acquire the next preview image may be shorter than the time that it takes to perform step SA1300 on one preview image.

The plurality of indicators extracted in step SA1300 may be information extracted to determine the adequacy of at least some of the above-described several evaluation indicators. The plurality of indicators extracted in step SA1300 may be information on some of the evaluation indicators set to be evaluated according to the photographing condition stored in the user terminal 100. As a specific example, the plurality of indicators may include position information of pupils, contour information of a face, etc., but are not limited thereto.

The plurality of indicators may be acquired through a landmark detection algorithm. For example, the user terminal 100 may determine the positions of the eyes in the preview image by using the landmark detection algorithm. Herein, the determined eye coordinates may be indicators related to the positions of the pupils.

The plurality of indicators may be acquired using a segmentation model. For example, the user terminal 100 may input the preview image to the segmentation model and may determine the positions of the eyes in the preview image. Herein, the determined eye areas may be indicators related to the positions of the pupils.

The plurality of indicators may be acquired through a bounding box detection algorithm. For example, the user terminal 100 may input the preview image to the bounding box detection algorithm and may determine the positions of the eyes and the face in the preview image. Herein, the determined eye areas may be indicators related to the positions of the pupils, and the determined face area may be an indicator related to a proportion that a face covers.

The indicators extracted in step SA1300 may be related to indicators for some of the above-described several evaluation indicators. When at least two indicators are extracted, the two indicators may be extracted by the same algorithm, or may be extracted by different algorithms.

The user terminal 100 may determine whether the extracted indicators are at appropriate positions in step SA1400. The terminal controller 150 may evaluate whether the extracted indicators are at appropriate positions in the preview image with reference to the photographing condition stored in the terminal storage part 130. In other words, the terminal controller 150 may determine whether the extracted indicators satisfy criteria.

According to several embodiments, the user terminal 100 may compare the extracted indicators to the positions of the photographing guidance. For example, when the user terminal 100 acquires coordinate values of pixels of the extracted indicators, it may be evaluated whether the acquired coordinate values and the coordinate value of the photographing guidance are spaced apart from each other within reference distances. Alternatively, according to several embodiments, the user terminal 100 may compare the extracted indicators to pre-stored criteria. For example, when the user terminal 100 acquires left eye coordinates and right eye coordinates analyzed using a landmark algorithm with the plurality of indicators, it may be evaluated whether the acquired eye coordinates are within a range of pixel values stored as appropriate positions.

The user terminal 100 may evaluate the left-right rotation angle of the face with respect to the acquired preview image in step SA1500. The terminal controller 150 may use an algorithm stored in the terminal storage part 130 to calculate the left-right rotation angle of the subject's face shown in the acquired preview image, and may determine whether the calculated left-right rotation angle of the face is within an appropriate range with reference to the photographing condition stored in the terminal storage part 130.

The user terminal 100 may perform step SA1500 on at least part of the acquired preview image. This is because the time that it takes to, after a preview image is acquired, acquire the next preview image may be shorter than the time that it takes to perform step SA1500 on one preview image.

The preview image on which step SA1300 is performed may be the same as the preview image on which step SA1500 is performed. Alternatively, the preview image on which step SA1300 is performed may be different from the preview image on which step SA1500 is performed. This is because the time that it takes to perform step SA1300 may be different from the time that it takes to perform step SA1500.

The left-right rotation angle of the face may be acquired through a left-right rotation angle detection algorithm (yaw estimation algorithm), or may be calculated by comparing the positions of body parts acquired using a landmark detection algorithm, but is not limited thereto.

The user terminal 100 may evaluate whether the left-right rotation angle of the face is within an appropriate range (that is, a first reference value). For example, evaluating whether the left-right rotation angle of the face is equal to or less than the first reference value may be based on whether the left-right rotation angle of the face is within an angle of ±2 degrees, but no limitation thereto is imposed.

The user terminal 100 may evaluate the up-down rotation angle of the face with respect to the acquired preview image in step SA1600. The terminal controller 150 may use an algorithm stored in the terminal storage part 130 to calculate the up-down rotation angle of the subject's face shown in the acquired preview image, and may determine whether the calculated up-down rotation angle of the face is within an appropriate range with reference to the photographing condition stored in the terminal storage part 130.

The user terminal 100 may perform step SA1600 on at least part of the acquired preview image. This is because the time that it takes to, after a preview image is acquired, acquire the next preview image may be shorter than the time that it takes to perform step SA1600 on one preview image.

The preview image on which step SA1500 is performed may be the same as the preview image on which step SA1600 is performed. Alternatively, the preview image on which step SA1500 is performed may be different from the preview image on which step SA1600 is performed. This is because the time that it takes to perform step SA1500 may be different from the time that it takes to perform step SA1600.

The up-down rotation angle of the face may be acquired through an up-down rotation angle detection algorithm (pitch detection algorithm, PDA), or may be calculated by comparing the positions of body parts acquired using a landmark detection algorithm, but is not limited thereto.

The user terminal 100 may evaluate whether the up-down rotation angle of the face is within an appropriate range (that is, a third reference value). For example, evaluating whether the up-down rotation angle of the face is equal to or less than the third reference value may be based on whether the up-down rotation angle of the face is within an angle of ±2 degrees, but no limitation thereto is imposed.

The user terminal 100 may evaluate the level of smiling with respect to the acquired image in step SA1700. The terminal controller 150 may use an algorithm stored in the terminal storage part 130 to analyze the subject's facial expression shown in the acquired preview image and to calculate the level of smiling, and may determine whether the calculated level of smiling is within an appropriate range with reference to the photographing condition stored in the terminal storage part 130.

The user terminal 100 may perform step SA1700 on at least part of the acquired preview image. This is because the time that it takes to, after a preview image is acquired, acquire the next preview image may be shorter than the time that it takes to perform step SA1700 on one preview image.

The preview image on which step SA1700 is performed may be the same as the preview image on which step SA1300 is performed. Alternatively, the preview image on which step SA1700 is performed may be different from the preview image on which step SA1300 is performed. This is because the time that it takes to perform step SA1700 may be different from the time that it takes to perform step SA1300.

The level of smiling may be acquired through a facial expression analysis algorithm (face reader), or may be calculated by comparing the positions of body parts acquired using a landmark detection algorithm, but is not limited thereto.

The user terminal 100 may evaluate whether the level of smiling on the face is within an appropriate range (that is, a second reference value). Herein, the appropriate range (that is, the second reference value) may be an appropriate range that is set to prevent the shapes of the eyes from changing as the person's expression become happy, which obstructs diagnosis accuracy. For example, evaluating whether the level of smiling is equal to or less than the second reference value may be based on whether the level of smiling is equal or less than 0.1, but no limitation thereto is imposed.

When it is determined that all the evaluation indicators set to be evaluated according to the photographing condition stored in the user terminal 100 are satisfied, the user terminal 100 may capture an image in step SA1800.

Even though all the evaluation indicators related to the photographing guidance provided in step SA1100 are satisfied, the user terminal 100 dose not capture an image when it is not determined that all the evaluation indicators set to be evaluated according to the stored photographing condition are satisfied. In other words, the user terminal 100 determines whether all the evaluation indicators to be evaluated according to the photographing condition are satisfied, without depending on the evaluation indicators provided with the photographing guidance.

When it is determined that all the evaluation indicators set to be evaluated according to the photographing condition stored in the user terminal 100 are satisfied with respect to one preview image, the user terminal 100 may capture an image in step SA1800. Alternatively, before capturing an image in step SA1800, when it is determined that each of the evaluation indicators set to be evaluated according to the photographing condition stored in the user terminal 100 is satisfied, the user terminal 100 may capture an image in step SA1800.

Capturing the image in step SA1800 may mean that the preview image acquired by the user terminal 100 immediately after it is determined that the condition is satisfied is stored as a captured image, or may mean that the preview image when it is determined whether the condition is satisfied is stored as a captured image by the user terminal 100. In the meantime, instead of the operation of automatically capturing an image, the user terminal 100 may activate a photographing button or provide a notification so that the user is capable of taking an image when it is determined that the photographing condition is satisfied.

Hereinafter, for convenience of description, although it is described that the user terminal 100 takes a picture when a condition according to each embodiment is satisfied, modifications may be made, for example, a photographing button is activated or a notification is provided to take a picture.

In addition, in several embodiments, the user terminal 100 may further perform the step of evaluating ambient brightness before the image is captured. The terminal controller 150 may determine whether ambient brightness is in an appropriate range through a terminal sensor part (not shown, for example, an ambient light sensor).

The user terminal 100 may evaluate whether ambient brightness is within an appropriate range (that is, a fourth reference value). Herein, the appropriate range (that is, the fourth reference value) may include: an appropriate minimum criterion set to have the brightness enough to enable image analysis even without flashing; and an appropriate maximum criterion set to have the brightness not to interfere with color analysis of the captured image. For example, evaluating whether ambient brightness is equal to or less than the fourth reference value may be based on whether the ambient brightness in a range of 100 to 1000 lux, but no limitation thereto is imposed.

In addition, in several embodiments, the user terminal 100 does not perform photographing when it is determined that at least one of the several evaluation indicators determined based on the preview image does not satisfy the pre-stored condition. Herein, information on the unsatisfied evaluation indicator may be provided. Herein, the provided information may be in the form of reporting the unsatisfied evaluation indicator, or in the form of informing the user of a desirable action to satisfy the unsatisfied evaluation indicator. For example, when it is determined that the level of smiling of the face determined based on the preview image exceeds a predetermined criterion, the user terminal 100 may provide a message "do not smile" through the display.

In addition, although the overall operation has been described in the above-described embodiment assuming that the photographing guidance is provided, the image acquisition method may be performed with the step of providing the photographing guidance omitted. Separately, the eye disease management system 10 described in the present specification needs to acquire an image in a precisely controlled environment, and thus, the user terminal 100 appropriately induces the user's action through the photographing guidance, thereby performing more improved eye disease management.

In addition, according to another embodiment, the above-described operation of the user terminal 100 may be performed by the eye disease management server 200. The eye disease management server 200 may store therein the following: an algorithm for extracting a plurality of indicators, and a related criterion; an algorithm for detecting an up-down rotation angle, and a related criterion; an algorithm for detecting a left-right rotation angle, and a related criterion; and an algorithm for detecting the level of smiling, and a related criterion. The user terminal 100 may serve as an interface for receiving and providing data in terms of the relation with a user. The user terminal 100 and the eye disease management server 200 are linked in real time, and according to the independent operation of the eye disease management server 200, the user terminal 100 may provide appropriate photographing guidance and may acquire a captured image to transmit the image to the eye disease management server 200.

Figure 6:
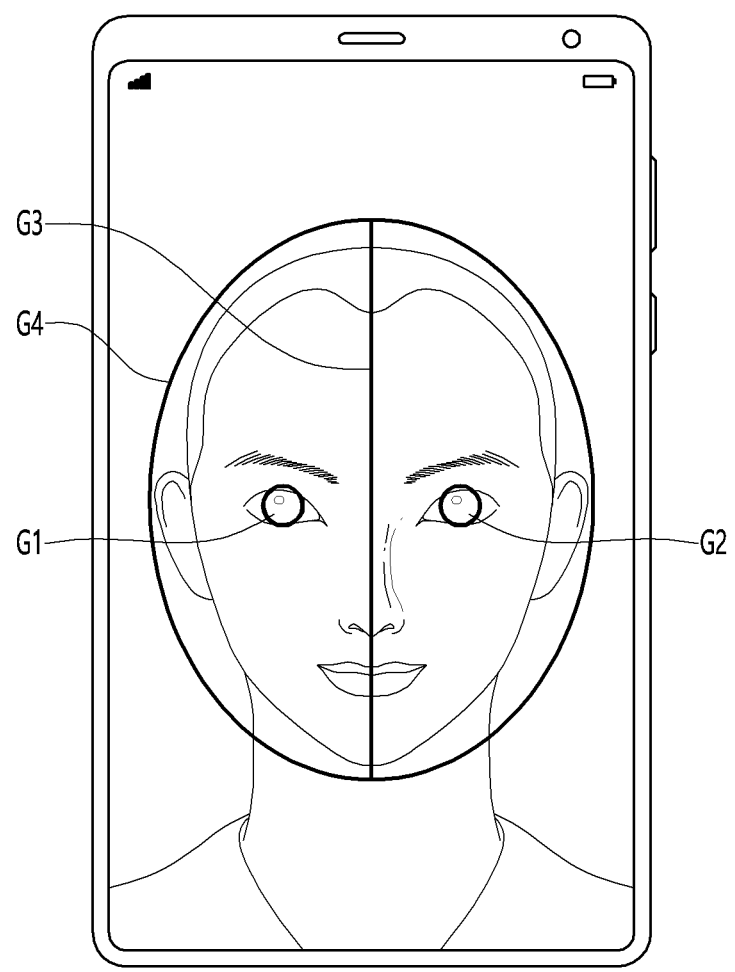
FIG. 6 is a diagram illustrating the forms and operation of photographing guidance provided according to an embodiment.

FIG. 6 is a diagram illustrating the forms and operation of photographing guidance provided according to an embodiment. Hereinafter, a description will be given assuming that the input/output module 140 is a display of a smartphone.

Referring to FIG. 6, the user terminal 100 according to an embodiment may provide fixed photographing guidance.

The photographing guidance may include a first guidance G1, a second guidance G2, a third guidance G3, and a fourth guidance G4. The first guidance G1 may be output to show an appropriate position of the subject's right eye. The second guidance G2 may be output to show an appropriate position of the subject's left eye. The third guidance G3 may be output to show an appropriate left-right rotation angle of the subject's face. The fourth guidance G4 may be output to show an appropriate coverage proportion for the subject's face.

The first guidance G1 may be output to directly or indirectly show the appropriate position of the subject's right eye. For example, the first guidance G1 may be output at the point at which the subject's right eye needs to be positioned, thereby helping the user to align his or her right eye with the first guidance G1. As shown in the drawing, the first guidance G1 may have a shape that shows the edge of the iris area when the subject's eye is at the appropriate position. Alternatively, the first guidance G1 may have a shape that shows the position of the pupil when the subject's eye is at the appropriate position or that shows the outline of the subject's eye.

As a specific example, the first guidance G1 may be provided in a cross shape. When the first guidance G1 is provided in the cross shape, the first guidance G1 may give guidance such that an image in which the center of the eye is placed at an appropriate position is captured without a pupil sensor. In other words, when the first guidance G1 is provided in the cross shape, the first guidance G1 may perform a function of inducing the user to match the center of the iris area of his or her left eye to the intersection point of the cross shape. Accordingly, an appropriate diagnostic image may be acquired to achieve high-accuracy analysis.

The second guidance G2 may be output to directly or indirectly show the appropriate position of the subject's left eye. The second guidance G2 is intended to show a different part from the first guidance G1, but may be provided in the same or similar shape. In other words, when the first guidance G1 is output to show the right pupil in a cross shape, the second guidance G2 may be output to show the left pupil in a cross shape.

The first guidance G1 and the second guidance G2 may be symmetrically provided on the display. The first guidance G1 and the second guidance G2 may be provided to be symmetrical with respect to the third guidance G3.

The third guidance G3 may be output to directly or indirectly show the left-right rotation angle of the subject's face. The third guidance G3 may show the left-right rotation angle of the face numerically, or may show the left-right rotation angle of the face as a vertical line extending along the length of the display. Herein, the vertical line may be a vertical line that passes through the area at which the nose in the face needs to be positioned when the subject's both eyes respectively correspond to the first guidance G1 and the second guidance G2 and the left-right rotation angle of the face is an angle of 0 degrees.

The fourth guidance G4 may be output to directly or indirectly show the appropriate proportion (portion) that the subject's face makes up in the image. The fourth guidance G4 shows the area in which the subject's face needs to be positioned in a circle shape or show the distance between the subject's face and the user terminal 100 so as to give guidance such that an image showing the state the subject's face makes up in the image is captured.

The first guidance G1, the second guidance G2, and the fourth guidance G4 may be associated with the evaluation indicators to be determined in step SA1400 described above. The third guidance G3 may be associated with the evaluation indicator to be determined in step SA1500 described above.

According to an embodiment, the user terminal 100 may provide a real-time photographing guidance RG together that is generated on the basis of information acquired by analyzing the fixed photographing guidance and the preview image.

The real-time photographing guidance RG may be generated for the evaluation indicator(s) related to the photographing guidance provided to the user terminal 100.

For example, real-time photographing guidance RG may be generated for all the evaluation indicators related to the photographing guidance provided by the user terminal 100. When the user terminal 100 provides photographing guidance for four evaluation indicators, real-time photographing guidance RG for the four evaluation indicators may be provided. As another example, a real-time photographing guidance RG may be generated for some of the evaluation indicators related to the photographing guidance provided by the user terminal 100. When the user terminal 100 provides photographing guidance for four evaluation indicators, real-time photographing guidance RG for two of the evaluation indicators may be provided.

A real-time photographing guidance RG may be provided in a shape corresponding to a photographing guidance. In other words, when a photographing guidance is in the shape of a vertical line, a real-time photographing guidance RG corresponding thereto may also be in the shape of a vertical line. When a photographing guidance is in a cross shape, a real-time photographing guidance RG corresponding thereto may also be in a cross shape.

At least one characteristic of a real-time photographing guidance RG may be changed according to whether a corresponding evaluation indicator is satisfied. When it is determined that the evaluation indicator corresponding to the real-time photographing guidance RG satisfies a pre-stored criterion, the user terminal 100 provides the real-time photographing guidance RG by changing the previously provided characteristic thereof, thereby enabling the user to easily recognize whether the condition is satisfied. The change in the characteristic may be a change from a dotted line to a solid line, a change in color, or a change in the thickness of the line, but is not limited thereto.

According to an embodiment, the user terminal 100 may analyze a preview image to acquire values (for example, the positions of the pupils and the left-right rotation angle of the face) corresponding to evaluation indicators, and may evaluate whether the values corresponding to the evaluation indicators satisfy criteria, and may provide real-time photographing guidance RG on the basis of the evaluated values.

According to another embodiment, the user terminal 100 may analyze a preview image to acquire values (for example, the positions of the pupils and the left-right rotation angle of the face) corresponding to evaluation indicators, and may provide corresponding real-time photographing guidance RG, and may compare the real-time photographing guidance RG with photographing guidance to evaluate whether the values corresponding to the evaluation indicators satisfy criteria.

Figure 7A:
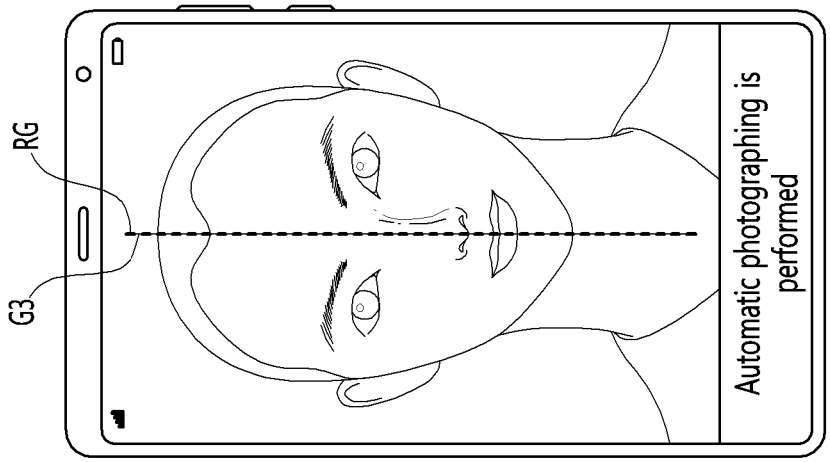
FIGS. 7A and 7B are diagrams illustrating the forms and operation of a real-time photographing guidance provided according to an embodiment.
Figure 7B:
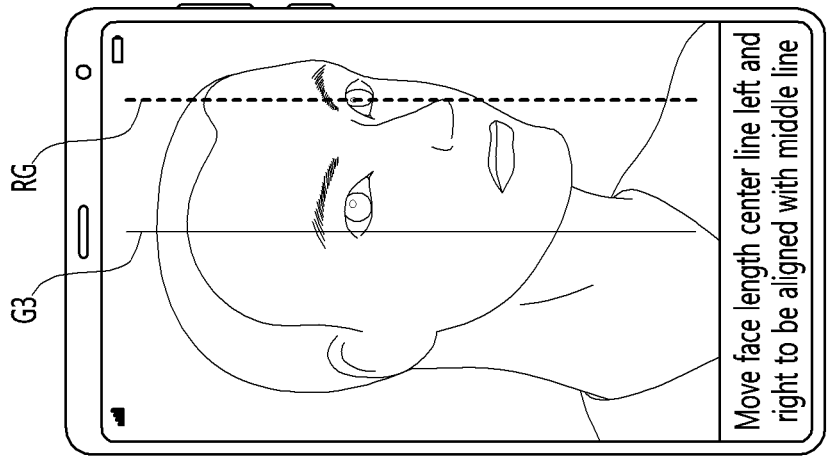

FIGS. 7A and 7B are diagrams illustrating the forms and operation of a real-time photographing guidance provided according to an embodiment. Hereinafter, described will be the operation of providing a third guidance G3 and a real-time guidance RG associated with the third guidance G3 through the user terminal 100.

According to an embodiment, the third guidance G3 may be provided in the shape of a vertical line. According to several embodiments, the third guidance G3 may be realized in such a way that a left-right rotation angle of a face is numerically provided, but there is a problem that it is not intuitively understood how the user should correct the posture. To solve this, like the third guidance G3, a left-right rotation angle of a face may be shown as a vertical line on the display. For example, the third guidance G3 may be provided as a vertical line that passes through the center with respect to the width of the display and extends along the length of the display.

While the third guidance G3 is provided as a fixed photographing guidance, the user terminal 100 may provide the real-time photographing guidance RG for the left-right rotation angle of the face.

When the left-right rotation angle of the face in the preview image is an angle of 0 degrees, the real-time photographing guidance RG may be provided as the vertical line that passes through the center of the width of the display and extends along the length of the display. When the left-right rotation angle of the face in the preview image is an angle of 90 degrees, the real-time photographing guidance RG may be provided as the vertical line that passes through a quarter point with respect to the width of the display and extends along the length of the display. The user terminal 100 stores a position of a vertical line for each left-right rotation angle of a face to equally show a point of the width of the display for each left-right rotation angle of a face in a preview image. A real-time photographing guidance RG may be provided in the shape of a vertical line extending along the length of the display according to a left-right rotation angle of a face.

Referring to FIG. 7A, the user terminal 100 may acquire a preview image while a third guidance G3 is provided. The acquired preview image may be analyzed to calculate a left-right rotation angle of the face, and a real-time photographing guidance RG corresponding to the calculated left-right rotation angle of the face may be provided.

The subject's face looks to the left side, so the real-time photographing guidance RG is positioned on the right side with respect to the width of user terminal 100 compared to the third guidance G3. Herein, the acquired left-right rotation angle of the face does not satisfy an appropriate range (that is, the first reference value), the real-time photographing guidance RG is shown as a dotted line.

Since the left-right rotation angle of the face in the preview image does not satisfy the first reference value, the user terminal 100 may provide the action that the user needs to perform to satisfy the first reference value, through the display. For example, an additional photographing guidance provided may be "move the face length center line left and right to be aligned with the middle line".

Referring to FIG. 7B, the subject's face looks to the front, so the real-time photographing guidance RG is positioned at the center with respect to the width of the user terminal 100 as the third guidance G3 is. The acquired left-right rotation angle of the face satisfies the appropriate range (that is, the first reference value), the real-time photographing guidance RG is shown as a solid line.

Since the left-right rotation angle of the face in the preview image satisfies the first reference value, the user terminal 100 may provide the user with information optionally. For example, while performing automatic photographing, the user terminal 100 may provide "automatic photographing is performed" through the display.

When an image for eye disease management is acquired, the user terminal 100 may transmit the image to the eye disease management server 200. Alternatively, when an image for eye disease management is acquired, the user terminal 100 may conduct image analysis. A method of predicting the possibility of eye disease by analyzing an image and of providing hospital visit guidance to a user on the basis of the possibility will be described later.

When an image for eye disease management (for example, prediction) is acquired, the user terminal 100 may output the image through the display. For example, when an image is acquired, the user terminal 100 may analyze the image to determine the positions of the eyes in the image, may crop the image such that the image includes the eyes and the surrounding parts of the eyes, and may output the cropped image through the display.

In several embodiments, the eye disease management server 200 may perform the operation of analyzing the image to detect the eyes and of cropping the image such that the image includes the eyes and the surrounding parts of the eyes. Alternatively, the user terminal 100 may perform the operation of analyzing the image to detect the eyes and of cropping the image such that the image includes the eyes and the surrounding parts of the eyes.

To detect the eyes, the user terminal 100 and/or the eye disease management server 200 may store a detection algorithm therein. For example, the detection algorithm may be a landmark detection algorithm or a segmentation model, but is not limited thereto.

In the present embodiment, a captured image is provided to a user, so that the user is allowed to check once more with the naked eye whether the eye image is inappropriately captured. If necessary, re-photographing may be performed. Accordingly, it is possible to solve the deterioration in the accuracy of diagnosis due to inappropriateness of an image.

In addition, in the present embodiment, since the captured image is cropped and provided, the user is allowed to more concentrate on checking the eyes when checking the image with the naked eye. Accordingly, it is possible to solve the deterioration in the accuracy of diagnosis due to inappropriateness of an image.

Figure 8:
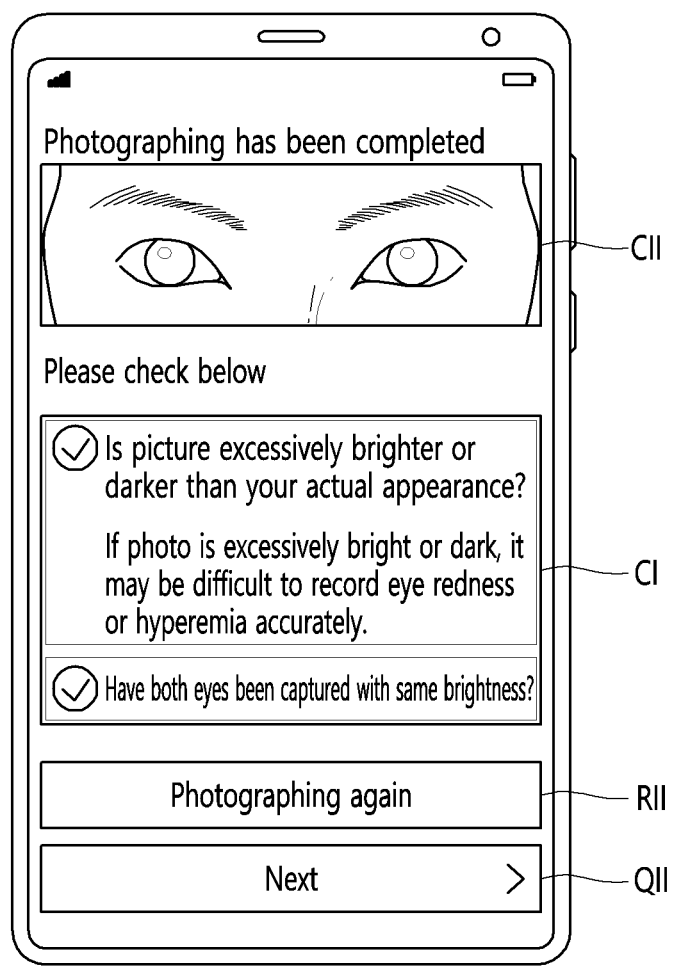
FIG. 8 is a diagram illustrating a display screen after taking an image with a user terminal according to an embodiment.

FIG. 8 is a diagram illustrating a display screen after taking an image with a user terminal according to an embodiment.

The user terminal 100 may provide a cropped image interface CII, a confirmation interface CI, a rephotographing interface RII, and a question input interface QII through the display.

The cropped image interface CII shows a partial area of the captured image, wherein the partial area may be an area including the eyes.

The confirmation interface CI may be an interface for checking whether the image is excessively brighter or darker than the actual appearance and whether the both eyes are captured with the same brightness because it is important to maintain an appropriate brightness in eye disease analysis. The confirmation interface CI may further include an area for receiving a response for each item. For example, a response area for whether the image is excessively brighter or darker than the actual appearance and a response area for whether the both eyes are captured with the same brightness may be provided through the display.

The rephotographing interface RII may be a selection interface provided for the user to perform a rephotographing function when the user wants to perform rephotographing after checking the cropped image and/or the confirmation items. The rephotographing interface RII is activated regardless of whether there are user inputs corresponding to the response areas of the confirmation interface CI. When the user terminal 100 acquires a user input of selecting the rephotographing interface RII, the re-photographing operation may be performed.

The question input interface QII may be a selection interface provided for the user to enter an input when the user wants to proceed to the next step after checking the cropped image and/or the confirmation items. The question input interface QII may be an interface activated when there are user inputs corresponding to the response areas of the confirmation interface CI. Specifically, when it is determined that appropriate responses are not input to the confirmation interface CI, the user terminal 100 may not perform an appropriate operation even when a user input of selecting the question input interface QII is acquired.

(2) Image Acquisition Method—Second Exemplary Embodiment

In order to predict thyroid eye disease accurately, it is important to acquire an image while the left-right rotation angle of the face and the up-down rotation angle of the face are maintained in appropriate ranges. This is because even when the same eye is photographed, the shape of the eye may be slightly changed according to the left-right rotation angle of the face and/or the up-down rotation angle of the face at the time point of capturing the image. This may act as a factor decreasing accuracy in predicting the possibility of thyroid eye disease or analyzing the degree of protrusion.

However, when an image is acquired using a smartphone, the CPU specifications (e.g., operation speed) of the smartphone needs to be considered in selecting an algorithm for analyzing a left-right rotation angle of a face and/or an up-down rotation angle of a face. Therefore, there is a demand for the development of a method of consistently monitoring a left-right rotation angle of a face and/or an up-down rotation angle of a face by using a low-throughput algorithm.

In particular, a left-right rotation angle of a face may be determined to some extent through symmetry of the face, but an up-down rotation angle of a face needs to be calculated on the basis of the positions of the eyes, nose, and mouth (for examples, body parts detected through a landmark detection algorithm) detected from the image. Therefore, a method of consistently monitoring an up-down rotation angle of a face needs to be developed.

Accordingly, described will be a method of selecting an image of a subject's correct posture as a reference image RI, generating and providing a reference guidance RG, and acquiring an image satisfying the reference guidance RG, thereby acquiring a captured image in which the left-right rotation angle and/or the up-down rotation angle of the face is consistently maintained.

However, in describing the embodiment below, the embodiment in which a reference guidance RG for giving guidance about an up-down rotation angle of a face is provided will be described as an example, and an embodiment in which a reference guidance RG for giving guidance about a left-right rotation angle of a face is provided will not be described in detail. However, a reference guidance RG for giving guidance about a left-right rotation angle of a face is implemented in such a way that reference guidance RG related to a plurality of reference guidance indicators spaced apart from each other along the width of a face are provided, and the operation may be performed similarly to the operation, which will be described later, of giving guidance about an up-down rotation angle, so it is understood that the embodiment not described in detail is sufficiently described to be implemented.

Similarly, an embodiment in which reference guidance RG for giving guidance about both a left-right rotation angle and an up-down rotation angle of a face are provided will not be described in detail, but is implemented in such a way that provided are reference guidance RG related to a plurality of reference guidance indicators spaced apart from each other along the length of a face and reference guidance RG related to a plurality of reference guidance indicators spaced apart from each other along the width of the face. The operation may be performed similarly to the operation, which will be described later, of giving guidance about an up-down rotation angle, so it is understood that the embodiment not described in detail is sufficiently described to be implemented.

Figure 9:
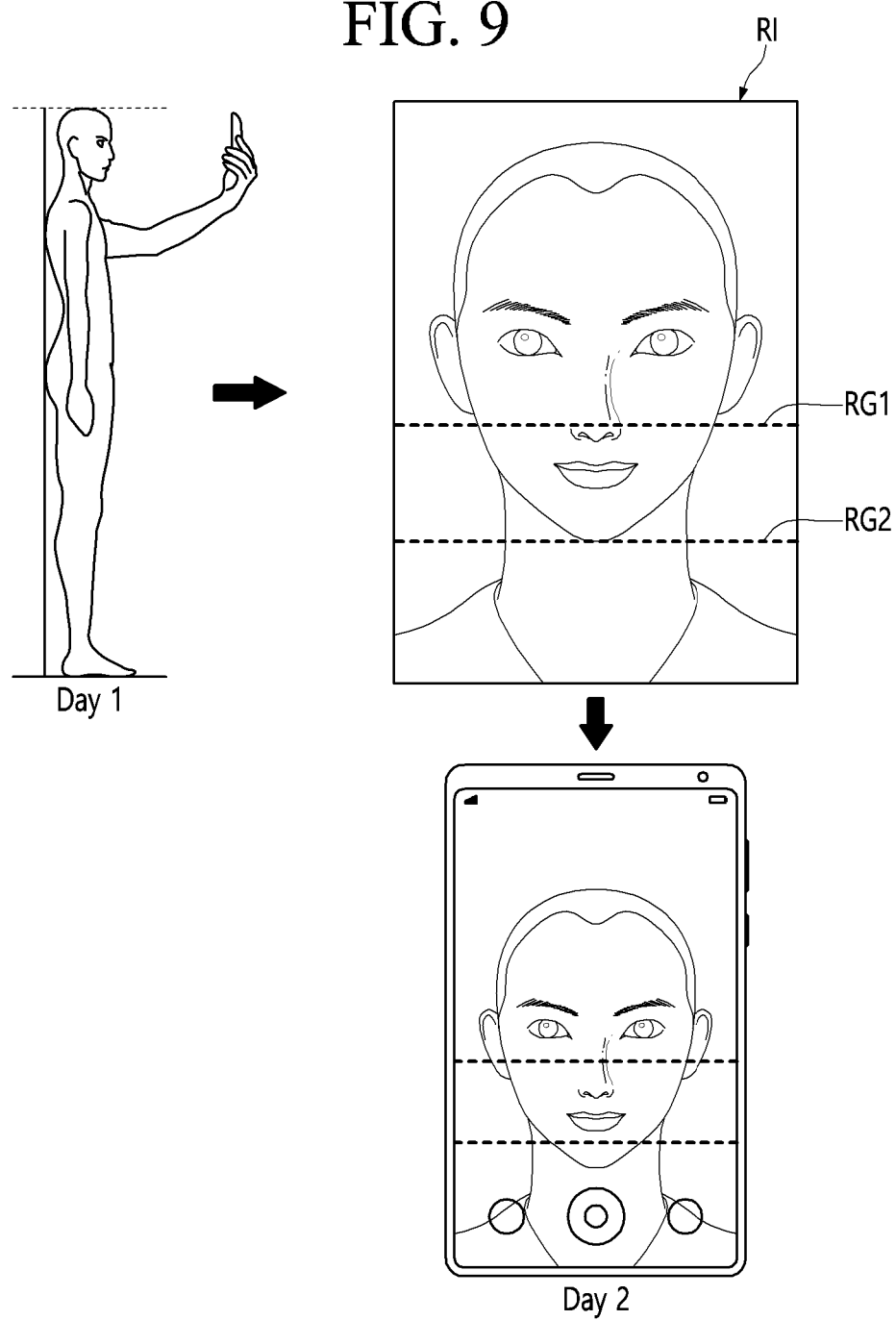
FIG. 9 is a diagram illustrating an image acquisition method according to an embodiment.

FIG. 9 is a diagram illustrating an image acquisition method according to an embodiment.

A user may take a reference image RI (see Day 1 of FIG. 9).

The reference image RI may be captured in an environment that the eye disease management system 10 suggests. For example, the reference image RI may be an image captured while the user leans his or her back against a wall. The reference image RI may be an image captured using the image acquisition method according to the first exemplary embodiment. The reference image RI may be an image captured by medical staff (for example, a nurse) in a hospital. The reference image RI may be an image post-evaluated as satisfying a photographing condition, among previously acquired diagnostic images (that is, captured images).

The reference image RI is analyzed to generate a reference guidance RG. A method of generating a reference guidance RG will be described in detail below.

A reference guidance RG (RI) may give guidance about at least two points. For examples, reference guidance RG may include a first reference guidance RG1 and a second reference guidance RG2.

The generated reference guidance RG may be stored in the terminal storage part 130 of the user terminal 100.

The user terminal 100 may provide the reference guidance RG (see Day 2 of FIG. 9). The user terminal 100 may provide the reference guidance RG at the time point of performing the image acquisition operation for eye disease management.

According to an embodiment, when the image acquisition operation is performed, the user terminal 100 provides the stored reference guidance RG through the display. According to another embodiment, when the image acquisition operation is performed, the user terminal 100 may provide the reference guidance RG and the photographing guidance together. The reference guidance RG are provided in the preview image.

Figure 10:
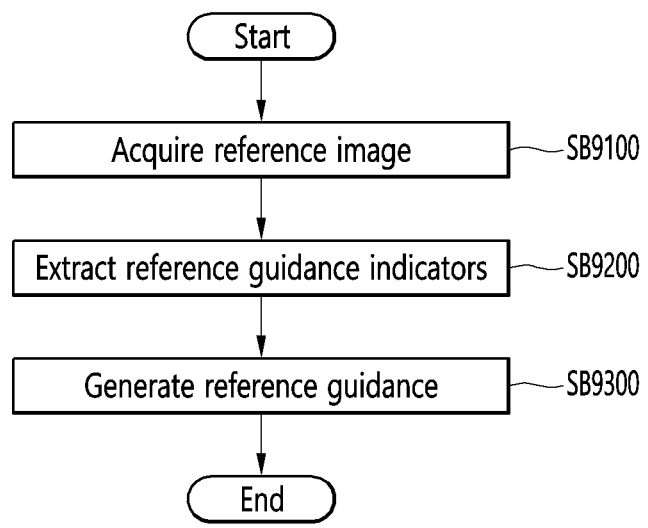
FIG. 10 is a diagram illustrating the operation of generating a reference guidance according to an embodiment.

FIG. 10 is a diagram illustrating the operation of generating a reference guidance according to an embodiment.

The user terminal 100 may acquire a reference image RI in step SB9100, may extract reference guidance indicators on the basis of the acquired reference image RI in step SB9100, and may generate reference guidance RG in step SB9300.

The acquiring of the reference image RI in step SB9100 may be performed through the image acquisition method according to an embodiment of the present specification. For example, the reference image RI may be acquired using the image acquisition method described with reference to FIG.

5. According to several embodiments, the reference image RI may be an image captured before the onset of thyroid eye disease.

The user terminal 100 may extract the reference guidance indicators by analyzing the reference image RI in step SB9200. The reference guidance indicators are related to body parts that may be shown in the front of a face, and at least two reference guidance indicators may be acquired.

The reference guidance indicators for giving guidance about the up-down rotation angle of the face are related to at least two points spaced apart from each other along the length of the face. The reference guidance indicators for giving guidance about the left-right rotation angle of the face are related to at least two points spaced apart from each other along the width of the face.

The reference guidance indicators may be position information corresponding to the tip of the nose and position information corresponding to an eye. In the present specification, "position information" is information for indicating a position in an image, and may be, for example, a coordinate value of a body part acquired through a landmark detection algorithm. Alternatively, the reference guidance indicators may be position information corresponding to the tip of the chin and position information corresponding to an eye. However, since the disease that the eye disease management system 10 monitors is thyroid eye disease, it is relatively preferable that because eyes may be changed in shape due to the protrusion of the eyeballs, the reference guidance indicators are set for the body parts not related to eyes.

The reference guidance indicators may be position information corresponding to the tip of the nose and position information corresponding to the lips. Alternatively, the reference guidance indicators may be position information corresponding to the tip of the chin and position information corresponding to the lips. However, the body parts related to the reference guidance indicators are monitored as a photographing condition in the operation of acquiring an image, so it is relatively preferable that the reference guidance indicators are set for the body parts not related to a part, such as lips, involved in big movement.

The reference guidance indicators may be position information corresponding to the tip of the nose and position information corresponding to the tip of the chin. The reference guidance indicators for giving guidance about the up-down rotation angle of the face may be position information corresponding to the tip of the nose and position information corresponding to the tip of the chin. However, without being limited thereto, the reference guidance indicators are body parts that may be shown in the front of a face, and may be selected to include at least two points.

The user terminal 100 may generate the reference guidance RG in step SB9300. The reference guidance RG may be in the form of showing, as dots on the display, the points corresponding to the reference guidance indicators extracted from the reference image RI, or may be shown in the form of the line passing through the points corresponding to the reference guidance indicators extracted from the reference image RI.

According to an embodiment, when the user terminal 100 provides the reference guidance RG to give guidance about the up-down rotation angle of the face, the reference guidance RG may include the following: a first reference guidance RG1 passing through the point corresponding to a first reference guidance indicator and extending along the width of the display; and a second reference guidance RG2 passing through the point corresponding to a second reference guidance indicator and extending along the width of the display.

According to another embodiment, when the user terminal 100 provides the reference guidance RG to give guidance about the left-right rotation angle of the face, the reference guidance RG may include the following: a first reference guidance RG1 passing through the point corresponding to a first reference guidance indicator and extending along the length of the display; and a second reference guidance RG2 passing through the point corresponding to a second reference guidance indicator and extending along the length of the display.

The user terminal 100 may store the reference guidance RG acquired through steps SB9100 to SB9300 in the terminal storage part 130. The stored reference guidance RG may be provided on the display each time the user terminal 100 performs the image acquisition operation for eye disease management. Alternatively, the user terminal 100 captures an image for predicting eye disease while the reference guidance RG are not provided, and analyzes the captured image to post-evaluate whether the image is a picture satisfying the reference guidance RG. When the post-evaluated captured image does not satisfy the criteria related to the reference guidance RG, the message "Although photographing condition is satisfied, whether the up-down rotation angle of the face is an angle of 0 degrees doubted because the picture has a different characteristic from the last picture" is shown through the display. Herein, the user terminal 100 may provide the rephotographing interface RII through the display.

According to an embodiment, when an eye disease management application 131 downloaded to the user terminal 100 is executed, the user terminal 100 may provide an interface to acquire a reference image RI and may generate reference guidance RG. In other words, at the time point when the eye disease management application 131 is first executed after downloaded to the user terminal 100, the user terminal 100 may provide the interface to acquire the reference image RI and may generate the reference guidance RG. Afterward, until a new reference image RI is acquired, the user terminal 100 may provide the stored reference guidance RG each time an image is captured through the eye disease management application 131. In the present embodiment, in particular, the reference guidance indicators do not include eyes. This is because as an eye protrudes, it may be analyzed that the distance between the eye and other indicators is close, and distortion may thus occur through the reference guidance RG.

According to another specific embodiment, when an image is captured through the eye disease management application 131 downloaded to the user terminal 100, the reference guidance RG generated by analyzing the previously captured image may be provided through the display. When an image is captured while the reference guidance RG are provided, the user terminal 100 may transmit the captured image to the eye disease management server 200. The user terminal 100 and/or the eye disease management server 200 may use the currently captured image to generate reference guidance RG again, and may provide the reference guidance RG acquired from the currently captured image, at the time point of capturing a next image for eye disease management. In other words, when a captured image is acquired, the user terminal 100 may store newly generated reference guidance RG in the terminal storage part 130 such that reference guidance RG are generated each time a captured image is acquired, and the reference guidance RG are provided when the next captured image is acquired.

According to an embodiment, when the image acquisition operation is performed, the user terminal 100 may provide the stored reference guidance RG through the display. According to another embodiment, when the image acquisition operation is performed, the user terminal 100 may provide the reference guidance RG and the photographing guidance together.

Figure 11:
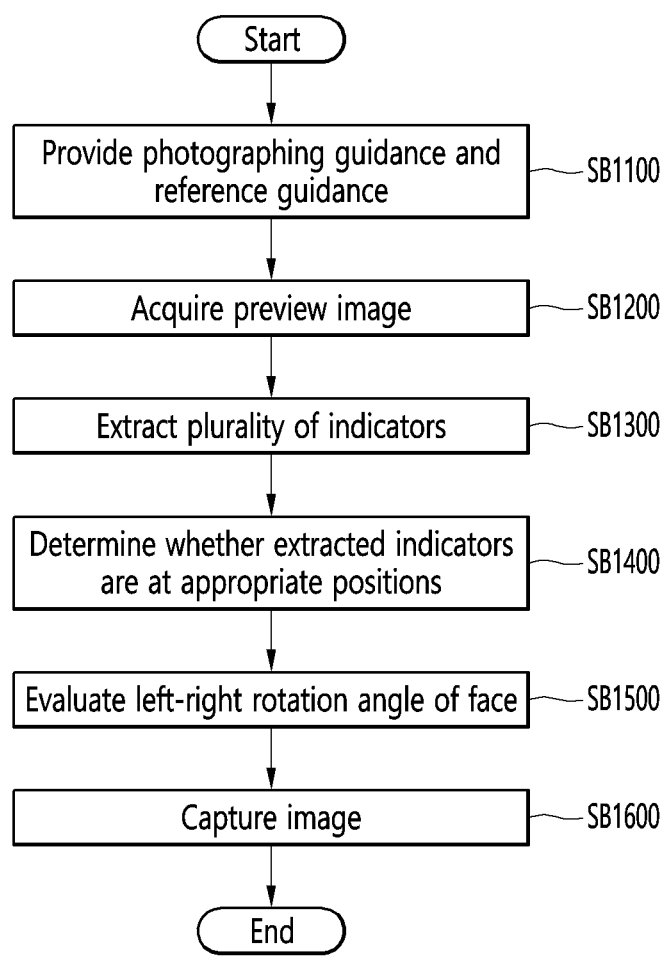
FIG. 11 is a diagram illustrating an image acquisition method according to an embodiment.

FIG. 11 is a diagram illustrating an image acquisition method according to an embodiment.

The user terminal 100 may provide photographing guidance and reference guidance RG in step SB1100, may acquire a preview image in step SB1200, may extract a plurality of indicators in step SB1300, may determine whether the extracted indicators are at appropriate positions in step SB1400, may evaluate a left-right rotation angle of the face in step SB1500, and may capture an image in step SB1600.

Herein, SB1200, SB1500, and SB1600 of FIG. 11 may be performed similarly to SA1200, SA1500, and SA1800 of FIG. 5, so a redundant description will be omitted.

Figure 12:
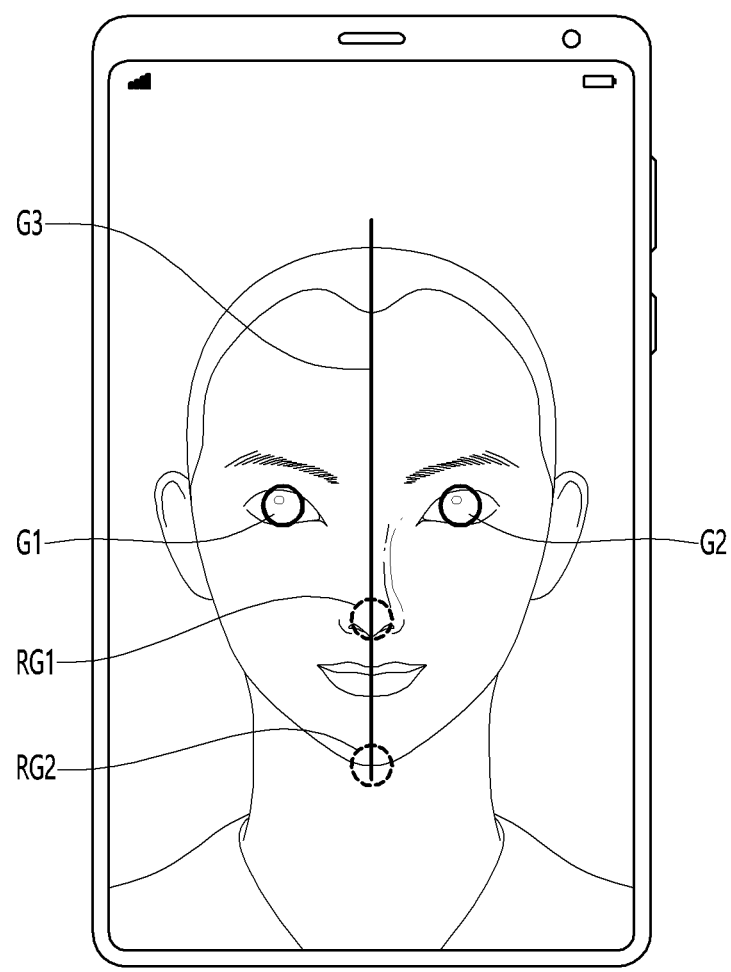
FIGS. 12, 13A and 13B are diagrams illustrating a display screen for providing photographing guidance and reference guidance according to an embodiment.

Referring to FIG. 12, the user terminal 100 may provide a first guidance G1, a second guidance G2, a third guidance G3, a first reference guidance RG1, and a second reference guidance RG2 through the display. Since the first guidance G1, the second guidance G2, and the third guidance G3 have been described with reference to FIG. 6 and the first reference guidance RG1 and the second reference guidance RG2 have been described with reference to FIG. 9, so a detailed description will be omitted.

The first reference guidance RG1 and the second reference guidance RG2 may be shown as the parallel horizontal lines as shown in FIG. 9, or may be shown to indicate positions corresponding to reference guidance indicators as dot guidance.

Referring back to FIG. 11, the user terminal 100 may acquire the preview image while the photographing guidance and the reference guidance RG are provided and may extract the plurality of indicators for the acquired preview image in step SB1300.

The user terminal 100 may extract the plurality of indicators related to the reference guidance RG from the preview image. The user terminal 100 may extract the plurality of indicators related to the reference guidance indicators from the preview image.

Herein, the plurality of indicators related to the reference guidance RG may be position information on the same body parts corresponding to the reference guidance RG and/or the reference guidance indicators, or may be position information on similar body parts. As a specific example, when the reference guidance RG are generated on the basis of position information of the tip of the nose, the plurality of indicators related to the reference guidance RG may be extracted from the position information of the tip of the nose. As another specific example, when the reference guidance RG are generated on the basis of position information of the eyes, the plurality of indicators related to the reference guidance RG may be extracted from position information of the pupils.

The user terminal 100 may extract one or a plurality of indicators corresponding to the photographing guidance, and may extract all of the plurality of indicators corresponding to the reference guidance RG. Specifically with reference to FIG. 12, the user terminal 100 may detect the both eyes corresponding to the first guidance G1 and the second guidance G2 to extract a plurality of indicators, and may detect the tip of the nose and the tip of the chin corresponding to the first reference guidance RG1 and the second reference guidance RG2 to extract a plurality of indicators.

The user terminal 100 may determine whether the extracted indicators are at appropriate positions in step SB1400. The terminal controller 150 may evaluate whether the extracted indicators are at appropriate positions in the preview image with reference to the photographing condition stored in the terminal storage part 130. In other words, the terminal controller 150 may determine whether the extracted indicators satisfy criteria.

The method of determining whether the extracted indicators related to the photographing guidance are at appropriate positions has been described with reference to FIG. 5, so a detailed description will be omitted.

According to several embodiments, the user terminal 100 may compare the extracted indicators related to the reference guidance RG with the positions of the reference guidance RG. For example, when the user terminal 100 acquires coordinate values of pixels of the extracted indicators related to the reference guidance RG, it may be evaluated whether the acquired coordinate values and the coordinate values of the reference guidance RG are spaced apart from each other within reference distances. Alternatively, according to several embodiments, the user terminal 100 may compare a distance between the extracted indicators with a distance between the reference guidance indicators. For example, when the user terminal 100 acquires the coordinates of the tip of the nose and the coordinates of the tip of the chin by using the plurality of indicators, the user terminal 100 may calculate the separation distance between the two points, and may evaluate whether the acquired separation distance and the separation distance between the reference guidance indicators differ within a predetermined range. When it is determined that the positions of the plurality of indicators satisfy the criteria in step SB1400 and the left-right rotation angle of the face satisfies the criterion in step SB1500, the user terminal 100 may capture the image in step SB1600. In this case, even though the up-down rotation angle of the face is not analyzed, a corresponding effect may be acquired.

The user terminal 100 may acquire the preview image while the photographing guidance and the reference guidance RG are provided. By analyzing the acquired preview image, an image may be captured or an additional guidance may be provided.

Figure 13A:
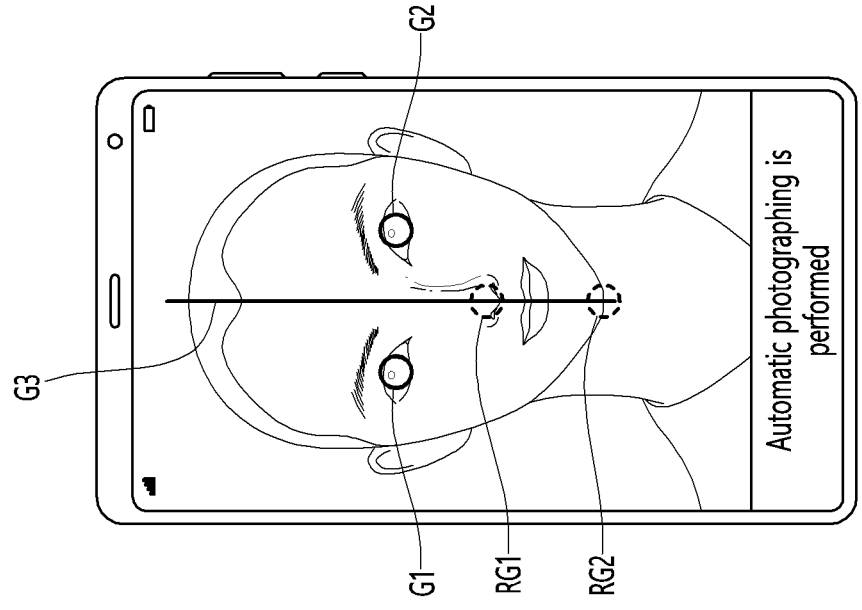

Referring to FIG. 13A, the subject's face looks down, so the distance between the tip of the nose and the tip of the chin extracted from the preview image is shorter than the distance between the first reference guidance RG1 and the second reference guidance RG2. The position information of the tip of the nose in the preview image corresponds to the first reference guidance RG1, but the position information of the tip of the chin in the preview image does not correspond to the second reference guidance RG2.

Since the up-down rotation angle of the face in the preview image does not satisfy the third reference value, the user terminal 100 may provide the action that the user needs to perform to satisfy the third reference value, through the display. For example, an additional photographing guidance provided may be "turn your face upward to align your nose and the tip of your chin with the guidance".

Figure 13B:
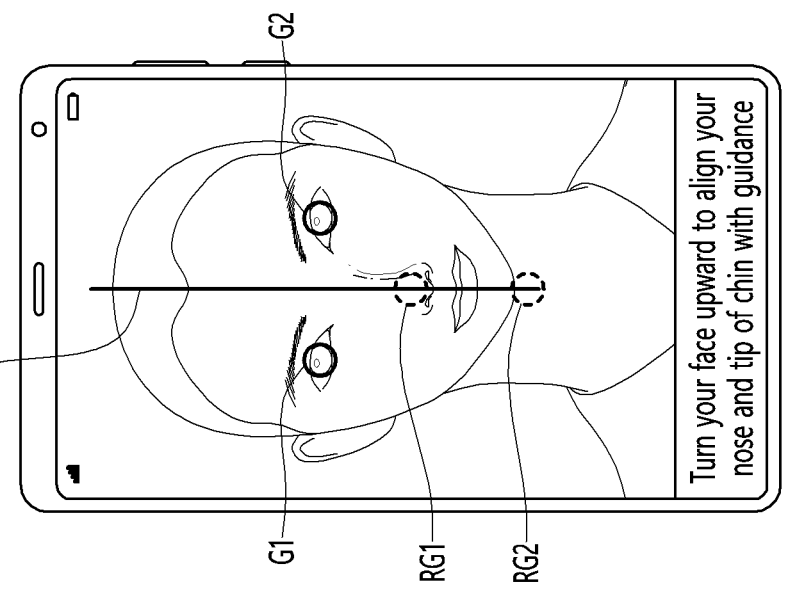

Referring to FIG. 13B, the subject's face looks to the front, so the distance between the tip of the nose and the tip of the chin extracted from the preview image is equal to the distance between the first reference guidance RG1 and the second reference guidance RG2. The position information of the tip of the nose in the preview image corresponds to the first reference guidance RG1, and the position information of the tip of the chin in the preview image corresponds to the second reference guidance RG2.

Since the up-down rotation angle of the face in the preview image satisfies the third reference value, the user terminal 100 may provide the user with information optionally. For example, while performing automatic photographing, the user terminal 100 may provide "automatic photographing is performed" through the display.

According to an embodiment, the above-described operation of the user terminal 100 may be performed by the eye disease management server 200. The user terminal 100 may serve as an interface for receiving and providing data in terms of the relation with a user. The user terminal 100 and the eye disease management server 200 are linked in real time, and according to the independent operation of the eye disease management server 200, the user terminal 100 may provide appropriate reference guidance RG and may acquire a captured image to transmit the image to the eye disease management server 200.

(3) Image Acquisition Method—Third Exemplary Embodiment

The thyroid eye disease management system 10 may perform the operation of predicting the possibility of thyroid eye disease for health management, and may perform the operation of monitoring the degree of protrusion caused by thyroid eye disease. In particular, in the case in which the thyroid eye disease management system 10 is used in clinical trials by a pharmaceutical company that develops a medication for thyroid eye disease, it is necessary to leave the 'treatment progress' according to taking medicine as data, so it is recommended that the operation of predicting thyroid eye disease and the operation of monitoring the degree of protrusion are performed simultaneously.

However, in order to check the degree of protrusion caused by thyroid eye disease with the naked eye or through an image analysis, a side image SI of a face is required, but it is difficult for an ordinary person to take a side image SI of the face accurately without medical staff's help. In particular, in the related art, in order to analyze the degree of protrusion of a face, images are acquired by photographing a face from the bottom upward with a camera. However, it is impossible to take images with consistency, and furthermore, patients do not want to record bottom-up pictures of their faces, so there is a difficulty in commercialization and service application.

Hereinafter, an image acquisition method of acquiring a front image and a side image SI of a face will be described in detail.

Figure 14:
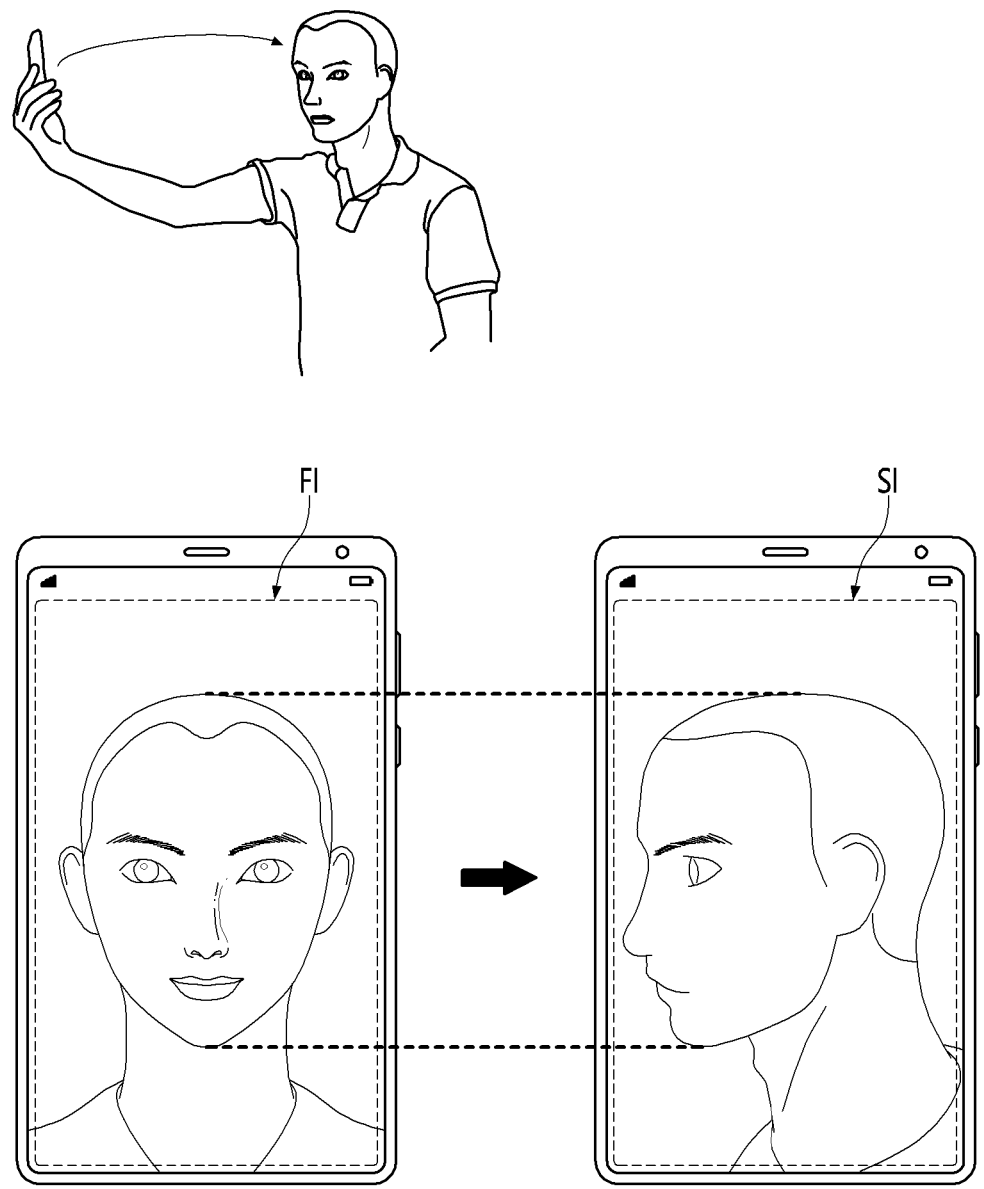
FIG. 14 is a diagram illustrating an image acquisition method according to an embodiment.

FIG. 14 is a diagram illustrating an image acquisition method according to an embodiment.

The present embodiment relates to a method in which a front image FI is first acquired, and panorama guidance is generated accordingly and provided, and a side image SI is acquired in a monitored state based on the panorama guidance.

In addition, in the present embodiment, described is that the user terminal 100 is induced to move according to the generated panorama guidance when a front image FI of a face is captured. In this case, the distance between the face and the user terminal 100 when a front image FI of the face is captured is maintained when a side image SI of the face is captured, so it is highly advantageous to be able to use the sizes of the irises in the front image FI in analyzing the degree of protrusion. Accordingly, it is possible to predict the degree of ocular proptosis by analyzing the side image SI.

Figure 15:
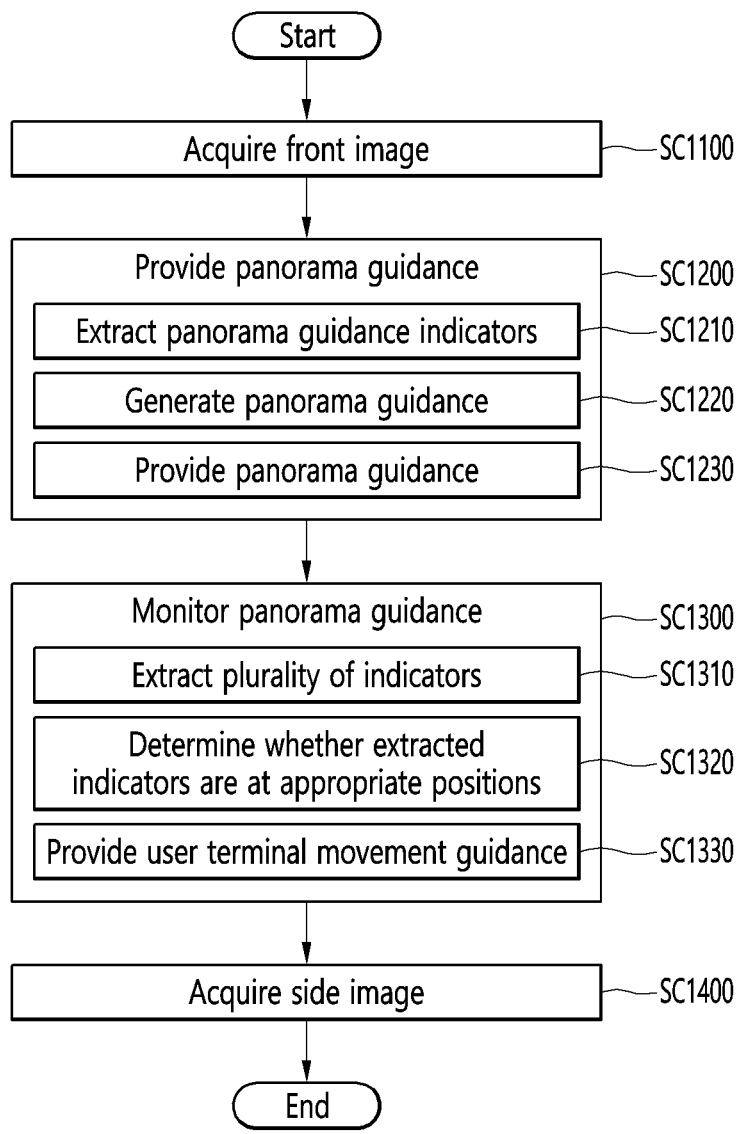
FIG. 15 is a diagram illustrating an image acquisition method according to an embodiment.

FIG. 15 is a diagram illustrating an image acquisition method according to an embodiment.

The user terminal 100 may acquire a front image FI in step SC1100. For example, the front image FI may be captured using the image acquisition method according to the first exemplary embodiment.

The front image FI may be acquired while guidance is given to satisfy a first photographing condition. For example, satisfying the first photographing condition may mean that a subject's both eyes are placed at predetermined areas in a first captured image. As another example, satisfying the first photographing condition may mean that a subject's both eyes are placed at predetermined areas in a first captured image and a left-right rotation angle of the subject's face does not exceed a predetermined first reference value. As still another example, satisfying the first photographing condition may mean that a subject's both eyes are placed at predetermined areas in a first captured image, a left-right rotation angle of the subject's face does not exceed a predetermined first reference value, and the subject's smile level based on facial expression information of the subject does not exceed a predetermined second reference value. As still another example, satisfying the first photographing condition may mean that a subject's both eyes are placed at predetermined areas in a first captured image, a left-right rotation angle of the subject's face does not exceed a predetermined first reference value, the subject's smile level based on facial expression information of the subject does not exceed a predetermined second reference value, and an up-down rotation angle of the subject's face does not exceed a predetermined third reference value. As still another example, satisfying the first photographing condition may mean that a subject's both eyes are placed at predetermined areas in a first captured image, a left-right rotation angle of the subject's face does not exceed a predetermined first reference value, the subject's smile level based on facial expression information of the subject does not exceed a predetermined second reference value, an up-down rotation angle of the subject's face does not exceed a predetermined third reference value, and ambient brightness does not exceed a fourth reference value.

After acquiring the front image FI, the user terminal 100 may provide panorama guidance in step SC1200. The panorama guidance provided by the user terminal 100 after the front image FI is acquired may be generated on the basis of the front image FI.

The panorama guidance may be generated on the basis of information extracted from the front image FI. According to an embodiment, the user terminal 100 may generate the panorama guidance on the basis of position information of a first point and a second point extracted from the front image FI, and may provide the panorama guidance.

The user terminal 100 may extract panorama guidance indicators in step SC1210. The panorama guidance indicators are the body parts that may shown in the front image FI of the face, and the body parts that may shown in the side image SI of the face. The panorama guidance indicators are related to at least two points spaced apart from each other along the length of the front face.

The panorama guidance indicators may be position information corresponding to the tip of the nose and position information corresponding to an eye. Alternatively, the panorama guidance indicators may be position information corresponding to the tip of the chin and position information corresponding to an eye. However, there is a change that when a left side image SI of the face is captured, the right eye is not detected, or when a right side image SI of the face is captured, the left eye is not detected, so it is preferable that the panorama guidance indicators do not include eyes.

The panorama guidance indicators may be position information corresponding to the tip of the nose and position information corresponding to the lips. Alternatively, the reference guidance indicators may be position information corresponding to the tip of the chin and position information corresponding to the lips. The body parts related to the panorama guidance indicators are monitored as a photographing condition until the side image SI is acquired, so it is relatively preferable that the panorama guidance indicators are set for the body parts not related to a part, such as lips, involved in big movement.

The panorama guidance indicators may be position information corresponding to the tip of the nose and position information corresponding to the tip of the chin. However, without being limited thereto, the panorama guidance indicators are body parts that may be shown in the front and the side of a face, and may be selected to include at least two points.

The user terminal 100 may generate the panorama guidance on the basis of the extracted panorama guidance indicators in step SC1220. The panorama guidance may be in the form of showing, as dots on the display, the points corresponding to the panorama guidance indicators extracted from the front image FI. For example, the panorama guidance may be in the form of the line passing through the points corresponding to the panorama guidance indicators extracted from the front image FI, or may be provided through indicators for showing positions.

According to an embodiment, when the user terminal 100 provides the panorama guidance, the panorama guidance may include the following: a first panorama guidance passing through the point corresponding to a first panorama guidance indicator and extending along the width of the display; and a second panorama guidance passing through the point corresponding to a second panorama guidance indicator and extending along the width of the display.

The user terminal 100 may provide the generated panorama guidance through the display in step SC1230. While the panorama guidance is provided through the display, the user terminal 100 may monitor the panorama guidance in step SC1300.

Specifically, the user terminal 100 may extract a plurality of indicators from a preview image in step SC1310. Herein, the plurality of indicators may be indicators corresponding to the panorama guidance indicators in step SC1210. Herein, the plurality of indicators may be position information on the same body parts corresponding to the panorama guidance and/or the panorama guidance indicators, or may be position information on similar body parts. As a specific example, when the panorama guidance is generated on the basis of position information of the tip of the nose, the plurality of indicators may be extracted from position information of the tip of the nose. As another specific example, when the panorama guidance is generated on the basis of position information of the eyes, the plurality of indicators may be extracted from position information of the pupils.

According to several embodiments, when the panorama guidance is monitored in step SC1300, the user terminal 100 may not evaluate whether the several evaluation indicators considered as a photographing condition when the front image FI is acquired are satisfied. For example, even though the positions of the both eyes are monitored when the front picture is captured, the positions of the both eyes may not be monitored when the user terminal 100 is moved while the panorama guidance is monitored.

According to several embodiments, when the panorama guidance is monitored in step SC1300, the user terminal 100 may continuously evaluate the up-down rotation angle of the subject's face in the preview image. In this case, it is possible to prevent a variable, for example, the separation distance between the tip of the subject's nose and the tip of the subject's chin is shortened according to the up-down rotation angle of the face, so the accuracy of monitoring whether the distance between the subject and the user terminal 100 is uniform is further improved.

The user terminal 100 may determine whether the extracted indicators are at appropriate positions in step SC1320. The user terminal 100 may provide a user terminal movement guidance in step SC1330.

The user terminal 100 may give guidance about the movement of the user terminal 100 so that a preview image corresponding to the panorama guidance is acquired.

The user terminal 100 may determine whether the extracted indicators are at appropriate positions in step SC1320.

According to several embodiments, the user terminal 100 may compare the extracted indicators to the positions of the panorama guidance in step SC1320. For example, when the user terminal 100 acquires the coordinate values of the plurality of indicators in step SC1320, it may be evaluated whether the acquired coordinate values and the coordinate values of the corresponding panorama guidance are spaced apart from each other within reference distances.

As a specific example, the user terminal 100 may extract position information of the tip of the nose and the tip of the chin in the face as panorama guidance indicators. While providing the panorama guidance generated using the panorama guidance indicators, the user terminal 100 may monitor whether the movement of the user terminal 100 corresponding to the panorama guidance is performed. The user terminal 100 may extract, from the preview image, the positions corresponding to the tip of the nose and the tip of the chin in the face, and may match the extracted positions of the tip of the nose and the tip of the chin to the panorama guidance indicators in a one-to-one manner to perform monitoring to achieve a difference within a predetermined error range.

The user terminal 100 may output a guidance for adjusting positioning between the user terminal 100 and the face. Specifically, when it is determined that a first point (for example, the tip of the chin) extracted from the preview image is moved from a first point extracted from the front image FI to the extent of exceeding a fifth reference value, the user terminal 100 may output a guidance for moving the user terminal 100 upward or downward with respect to the face. In addition, when it is determined that a second point (for example, the tip of the nose) extracted from the preview image is moved from a second point extracted from the front image FI to the extent of exceeding a sixth reference value, the user terminal 100 may output a guidance for moving the user terminal 100 upward or downward with respect to the face.

Alternatively, according to several embodiments, the user terminal 100 may compare a separation distance between the extracted indicator with a separation distance between the reference guidance indicators in step SC1320. For example, when the user terminal 100 acquires the coordinates of the tip of the nose and the coordinates of the tip of the chin of the plurality of indicators in step SC1320, the user terminal 100 may calculate the separation distance between the two points, and may evaluate whether the acquired separation distance and an initial separation distance between the panorama guidance indicators differ within a predetermined range.

As a specific example, the user terminal 100 may extract positions of the tip of the nose and the tip of the chin in the face as panorama guidance indicators. While providing the panorama guidance generated using the panorama guidance indicators, the user terminal 100 may monitor whether photographing according to the panorama guidance is performed. The user terminal 100 may extract, from the preview image, the positions of the tip of the nose and the tip of the chin in the face to calculate a separation distance, and may perform monitoring such that the separation distance and an initial separation distance between the panorama guidance indicators have a difference within a predetermined error range.

When it is determined that the difference is out of the predetermined error range, the user terminal 100 may output a guidance for adjusting the distance between the user terminal 100 and the face. Specifically, when it is determined that a vertical separation distance between a first point (for example, the tip of the chin) and a second point (for example, the tip of the nose) extracted from the preview image is larger than an initial separation distance (that is, positions corresponding to first and second points in the front image FI) to the extent of being out of a predetermined error range, the user terminal 100 may output a guidance for moving the user terminal 100 away from the face. Conversely, when it is determined that the vertical separation distance between the first point and the second point extracted from the preview image is smaller than the initial separation distance to the extent of being out of the predetermined error range, the user terminal 100 may output a guidance for moving the user terminal 100 close to the face.

The user terminal 100 may acquire a side image SI in step SC1400. The user terminal 100 may acquire the side image SI in step SC1400 while guidance is given to satisfy a second photographing condition.

In an environment in which panorama guidance monitoring is performed, when the user terminal 100 is moved to a position at which the side image SI of the face is acquire, the user terminal 100 may acquire the side image SI in step SC1400.

Satisfying the second photographing condition may be determined on the basis of an indicator for recognizing the side of a face. In addition, satisfying the second photographing condition may be determined as satisfying a criterion for performing panorama guidance monitoring.

For example, satisfying the second photographing condition may mean that a vertical separation distance between a first point and a second point extracted from a second captured image and an initial separation distance have a difference within a predetermined error range. Satisfying the second photographing condition may mean that a vertical separation distance between a first point and a second point extracted from a second captured image and an initial separation distance have a difference within a predetermined error range and the subject's ear is placed at a determined area in the second captured image. Satisfying the second photographing condition may mean that a vertical separation distance between a first point and a second point extracted from a second captured image and an initial separation distance have a difference within a predetermined error range and the subject's one eye is not detected in the second captured image.

Figure 16:
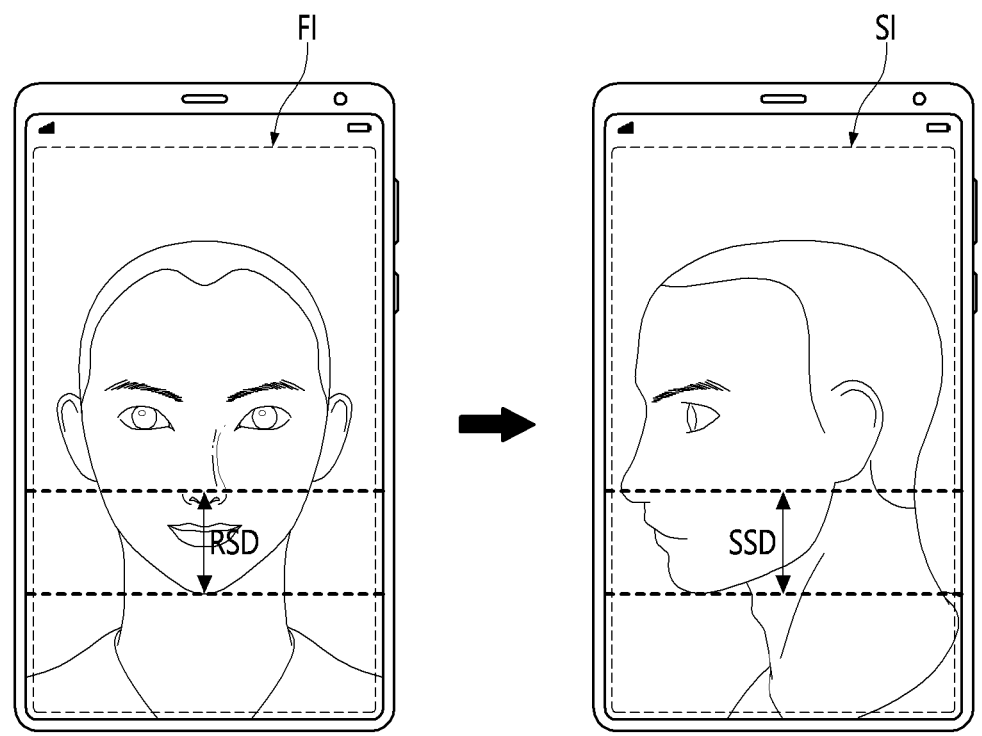
FIG. 16 is a diagram illustrating a front image and a side image according to an embodiment.

FIG. 16 is a diagram illustrating a front image and a side image according to an embodiment.

A reference separation distance RSD of a front image FI acquired using the image acquisition method according to the present embodiment and a side separation distance SSD of a side image SI have similar values. That is, the front and the side image SI may be acquired while the distance between the user terminal 100 and the subject is uniformly maintained at the time point when the front image FI is captured and at the time point when the side image SI is captured.

To perform a method, which will be described below, of analyzing the degree of ocular proptosis, required is a means for estimating the actual distance. It is found that the diameters of people's irises are nearly identical, so in the case of acquiring a front and a side image SI according to the present embodiment, the degree of ocular proptosis is estimated assuming that the diameters of the irises acquired from the front image FI are pre-stored lengths. Accordingly, the degree of ocular proptosis is estimated without a separate means for acquiring an absolute value.

The image acquisition method described with reference to FIGS. 14 to 16 may be performed to acquire a right side image SI of a face, or may be performed to acquire a left side image SI of a face. The image acquisition method may be performed twice to acquire a left side and right side images SIs of a face.

Through the image acquisition method described above, a front image FI of a face and a side image SI of the face may be acquired. Alternatively, through the image acquisition method described above, video images may be acquired including frames corresponding to a front image FI of a face, and frames corresponding to a side image SI of the face. Herein, the video images may be video images that are continuously captured starting from the time point when the front image FI of the face is acquired to the time point when the side image SI of the face is acquired. Alternatively, through the image acquisition method described above, a panoramic image edited to include a front image FI of a face and a side image SI of the face may be acquired.

According to an embodiment, the above-described operation of the user terminal 100 may be performed by the eye disease management server 200. The user terminal 100 may serve as an interface for receiving and providing data in terms of the relation with a user. The user terminal 100 and the eye disease management server 200 are linked in real time, and according to the independent operation of the eye disease management server 200, the user terminal 100 may provide appropriate panorama guidance and may acquire a front and a side image SI to transmit the images to the eye disease management server 200.

3. Operation of Eye Disease Management System—Image Analysis Method

(1) Image Analysis Method—First Exemplary Embodiment

Figure 17:
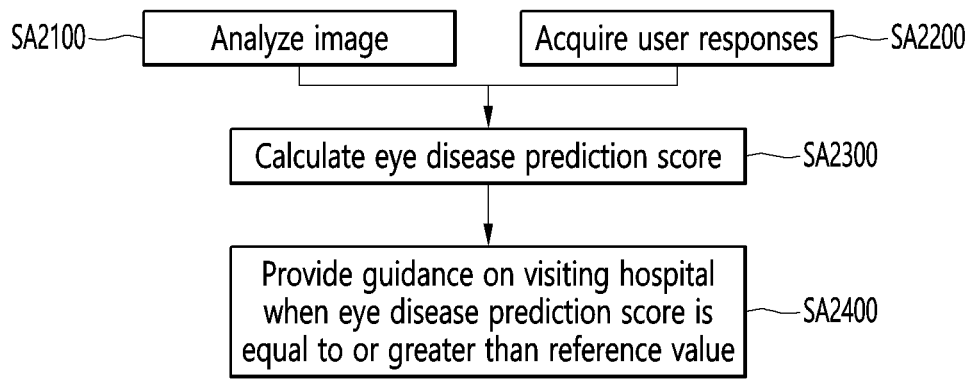
FIG. 17 is a flowchart illustrating a method of predicting thyroid eye disease according to an embodiment.

FIG. 17 is a flowchart illustrating a method of predicting thyroid eye disease according to an embodiment.

An image acquired by the user terminal 100 may be transmitted to the eye disease management server 200.

The eye disease management server 200 may perform image analysis using the received image in step SA2100. The values acquired through the image analysis may be prediction values for whether the person who is the subject in the received image has symptoms of conjunctival hyperemia, conjunctival edema, eyelid redness, eyelid edema, and lacrimal edema. For example, when the image include a facial image of the subject, the eye disease management server 200 may analyze the facial image to acquire information on whether conjunctival hyperemia is estimated to be present, whether conjunctival edema is estimated to be present, whether eyelid redness is estimated to be present, whether eyelid edema is estimated to be present, and/or whether lacrimal edema is estimated to be present.

A prediction value for at least one of conjunctival hyperemia, conjunctival edema, eyelid redness, eyelid edema, and lacrimal edema may be acquired through an artificial intelligence model. According to several embodiments, the eye disease management server 200 may acquire prediction values by using at least five artificial intelligence models, and each of the artificial intelligence models may be trained to output a prediction value for conjunctival hyperemia, conjunctival edema, eyelid redness, eyelid edema, or lacrimal edema. Herein, the image used as an input of the artificial intelligence models may be an image acquired by preprocessing, such as cropping, masking, inversion, and/or resizing, a facial image.

The user terminal 100 may transmit a user response to the eye disease management server 200. The user terminal 100 may output, through the input/output module 140, a user interface for acquiring each user response to whether the user has spontaneous retrobulbar pain and to whether the user has pain on an attempted upward or downward gaze. The eye disease management server 200 may acquire, on the basis of the received user responses, prediction values for spontaneous retrobulbar pain and pain on an attempted upward or downward gaze.

The eye disease management server 200 may use the prediction values acquired through the image analysis in step SA2100 and the prediction values acquired through the user responses in step SA2200, so as to calculate an eye disease prediction score in step SA2300. Herein, the eye disease prediction score is a value estimated with a technique, such as image analysis, of the eye disease management system for a clinical activity score, and may be calculated by estimating whether each of the following is present and giving a score of 1 for each presence: conjunctival hyperemia, conjunctival edema, eyelid redness, eyelid edema, lacrimal edema, spontaneous retrobulbar pain, and pain on an attempted upward or downward gaze.

When the eye disease prediction score is equal to or greater than a reference value, the eye disease management server 200 may guide the user to visit the hospital in step SA2400. The server 200 may provide the eye disease prediction score to the user terminal 100 in order to guide the user to visit the hospital. The server 200 may transmit necessary data so that the user terminal 100 outputs the eye disease prediction score and/or hospital visit guidance.

The user terminal 100 may output a message recommending that the patient visit the hospital and receive treatment. The user terminal 100 may recommend that the patient take a drug used for thyroid eye disease treatment. Without being limited thereto, the user terminal 100 may give guidance such that the patient performs a procedure necessary to treat thyroid eye disease.

Figure 18:
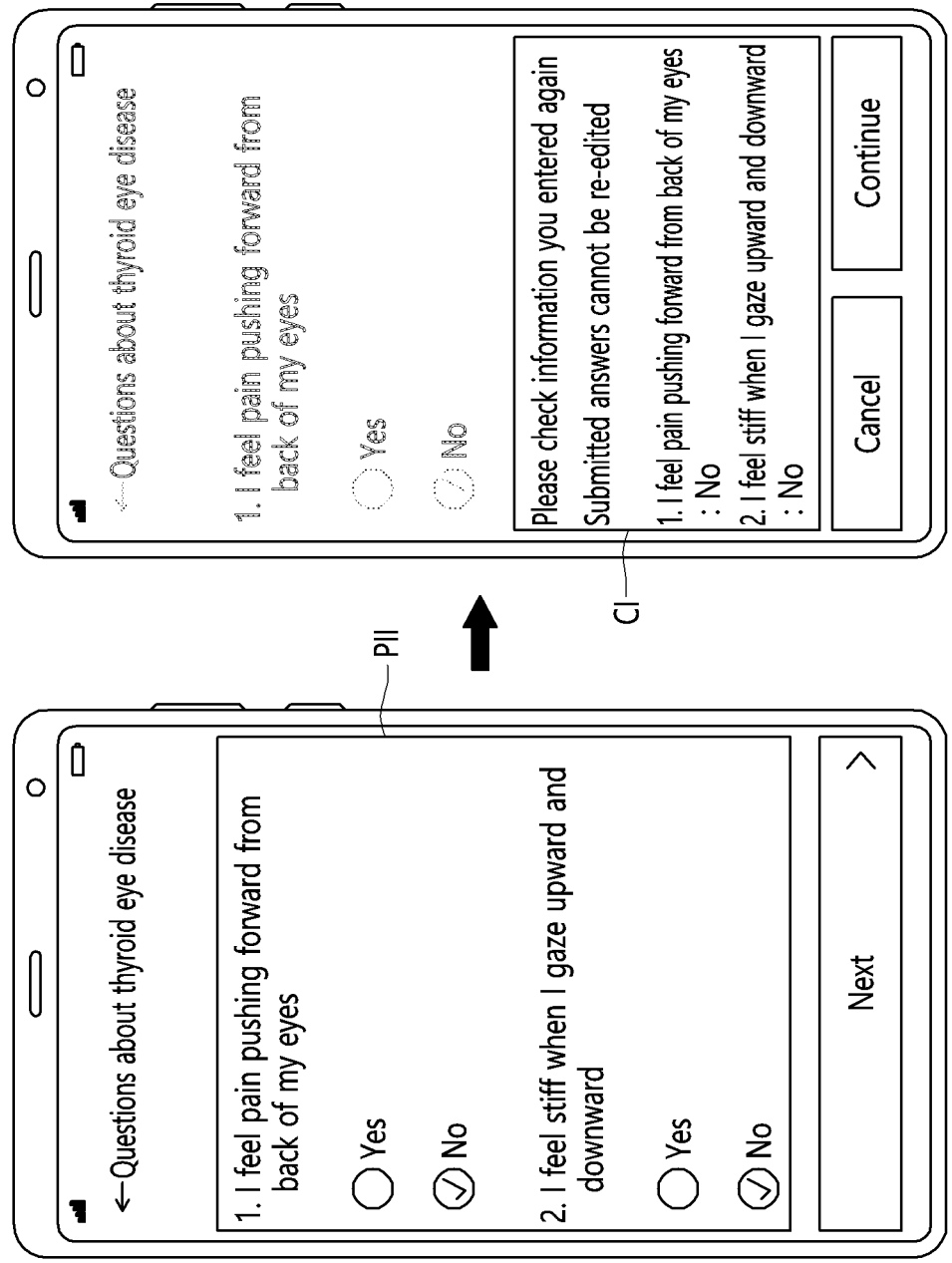
FIG. 18 is a diagram illustrating a display screen including a question input interface and a confirmation interface of a user terminal according to an embodiment.

FIG. 18 is a diagram illustrating a display screen including a question input interface and a confirmation interface of a user terminal according to an embodiment.

A question input interface PII may be an interface for acquiring each user response to whether the user has spontaneous retrobulbar pain and to whether the user has pain on an attempted upward or downward gaze. For example, "I feel pain pushing forward from the back of my eyes" and "I feel stiff when I gaze upward and downward" are output, and the interface for receiving the user's respective responses may be provided through the input/output module 140 of the user terminal 100.

When the user input for the two questions is acquired through the user terminal 100 and "Next" is pressed, a confirmation interface CI may be output.

The confirmation interface CI may perform a function of outputting the items selected in the question input interface PII by the user and confirming whether the items match the input intended by the user. The user's responses acquired through the question input interface PII are of high importance because the responses are used in predicting eye disease. Therefore, a 2-step input method is adopted to enable the user to confirm the responses once more and predict a result with high accuracy.

For the same reason, when the question input interface PII acquires only one response to either "I feel pain pushing forward from the back of my eyes" or "I feel stiff when I gaze upward and downward", switching to the confirmation interface CI may not be performed even though the button "Next" is pressed.

Figure 19:
FIG. 19 is a diagram illustrating indicators for predicting thyroid eye disease according to an embodiment.

FIG. 19 is a diagram illustrating indicators for predicting thyroid eye disease according to an embodiment.

According to another embodiment, whether to provide guidance on visiting a hospital for thyroid eye disease may be determined depending on whether the clinical activity score calculated out of a score of 7 is equal to or greater than a score of 3. However, in the present embodiment, described will be the case in which whether to provide guidance on visiting a hospital for thyroid eye disease may be determined depending on whether the clinical activity score calculated out of a score of 10 is equal to or greater than a score of 4.

Herein, the eye disease management server 200 may analyze the degree of protrusion, may calculate the angle of eyeball movement, and may acquire the estimated visual acuity.

A method of analyzing the degree of protrusion will be described in detail in "image analysis method—second exemplary embodiment" below.

The eyeball movement may be evaluated by analyzing video images. For example, a guidance is given to the user to move his or her eyes in eight directions while a front face image of the user is captured, and the angle of eyeball movement may be acquired on the basis of the position to which the maximum movement is made. The angle of eyeball movement may be calculated in such a way that an estimated value is calculated with the diameter of an eyeball of a person or the diameter of an iris of a person as a constant, considering the theory that the sizes of eyeballs and irises of people are generally similar. As a specific example, the diameter of an eyeball may be set to 24 mm, and the diameter of an iris may be set to 11 mm. Alternatively, the diameters of irises are set to vary according to race, sex, and age, and the angle of eyeball movement may be calculated.

Regarding the estimated visual acuity, the distance between the face and the user terminal 100 is estimated by comparing the sizes of the irises acquired from the front image FI of the face and the absolute sizes of the irises, and the sizes when the user does not correctly guess a letter output through the user terminal 100 are converted into the estimated distance between the face and the user terminal 100, thereby estimating visual acuity.

Alternatively, in order to exclude factors such as nearsightedness, farsightedness, etc., the distance between the user terminal 100 and the face may be set to about 3 m or 5 m, a letter in an appropriate size is output through the display, and it is evaluated whether the user guesses the letter correctly, thereby acquiring estimated visual acuity. Even in this case, the distance between the user terminal 100 and the face may be calculated on the basis of the sizes of the irises acquired from the front image FI of the face.

(2) Image Analysis Method—Second Exemplary Embodiment

Figure 20:
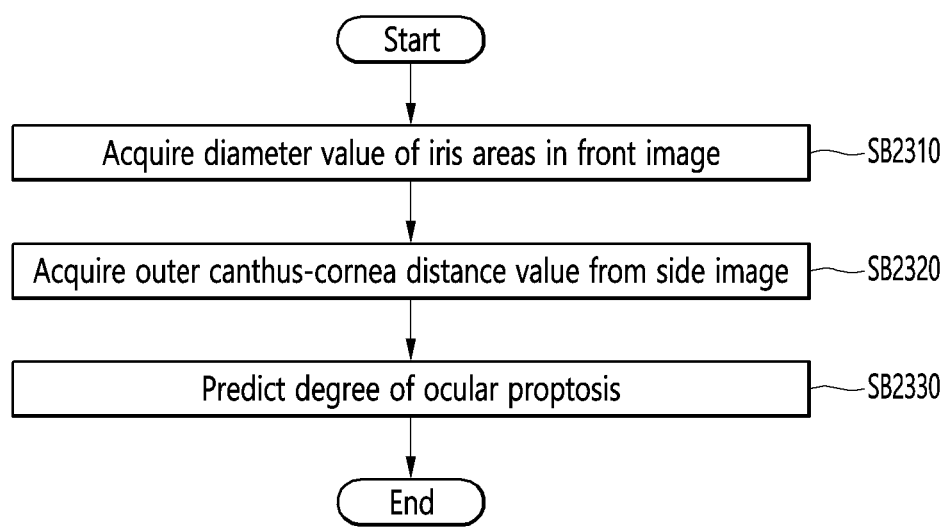
FIG. 20 is a diagram illustrating a method of predicting the degree of ocular proptosis by analyzing a side image of a face according to an embodiment.

FIG. 20 is a diagram illustrating a method of predicting the degree of protrusion by analyzing a side image of a face according to an embodiment.

The eye disease management server 200 may acquire a diameter value of iris areas in a front image FI in step SB2310. For example, the eye disease management server 200 may acquire a pixel value corresponding to the diameter of the iris areas through extraction of landmarks from the front image FI of the face. As another example, the eye disease management server 200 may acquire a pixel value corresponding to the diameter of the iris areas by using the front image FI of the face and a segmentation model. As still another example, the eye disease management server 200 may input the front image FI of the face to a model for predicting a diameter value of iris areas and may acquire a corresponding pixel value or estimated value of the diameter.

When the eye disease management server 200 acquires the pixel value corresponding to the diameter of the iris areas in the front image FI, an actual size value corresponding to one pixel may be calculated on the basis of a standard size of the iris areas and stored.

The eye disease management server 200 may acquire an outer canthus-cornea distance value from a side image SI in step SB2320. For example, the eye disease management server 200 may acquire pixel values corresponding to the outer canthus-cornea distances by using a segmentation model for the front image FI. As another example, the eye disease management server 200 may input the side image SI of the face to a model for predicting an outer canthus-cornea distance and may acquire a corresponding pixel value or an estimated value of the distance.

The eye disease management server 200 may predict the degree of ocular proptosis in step SB2330. The eye disease management server 200 may predict the degree of ocular proptosis considering the pixel values corresponding to the acquired outer canthus-cornea distances, and an actual size value of one pixel calculated on the basis of the standard size of the iris areas.

Figure 21:
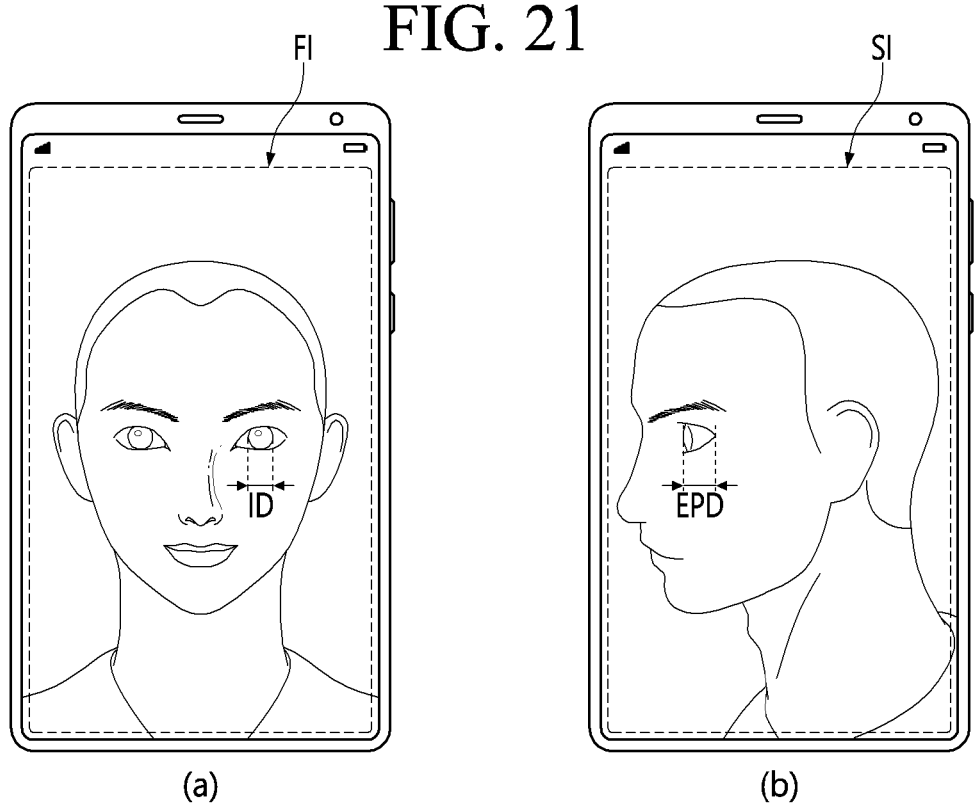
FIG. 21 is a diagram illustrating a diameter value of an iris area in a front image of a face and the degree of protrusion of an eyeball in a side image of the face according to an embodiment.

FIG. 21 is a diagram illustrating a diameter value of an iris area in a front image of a face and the degree of protrusion of an eyeball in a side image of the face according to an embodiment.

In the above-described operation in step SB2310, an estimated length of a diameter value ID of an iris area in the front image FI of the face may be calculated. In the above-described operation in step SB2320, an estimated length of an outer canthus-cornea distance in the side image SI of the face may be calculated.

The eye disease management server 200 may provide the date (and/or time) when the side picture of the face is acquired, together through the user terminal 100. The eye disease management server 200 may map the cropped image showing the outer canthus-cornea distance in the face to the date when the image is acquired and may provide a result of mapping so that the user is able to check the change in the degree of ocular proptosis through the user terminal 100.

The methods according to the above-described embodiments may be written as computer-executable programs, and may be implemented in a general-use digital computer that executes the programs by using a computer-readable recording medium. In addition, data structures, program instructions, or data files, which may be used in the embodiments of the present disclosure, may be recorded on a computer-readable recording medium through various means. Examples of the computer-readable recording medium may include all types of storage devices in which data readable by a computer system is stored. Examples of the computer-readable recording medium include: magnetic media such as hard disks, floppy disks, and magnetic tapes; optical media such as CD-ROMs and DVDs; magneto-optical media such as floptical disks; and hardware devices, such as ROM, RAM, flash memory, etc., which are particularly configured to store and implement program instructions. In addition, the computer-readable recording medium may be a transmission medium for transmitting signals designating program instructions, data structures, etc. Examples of the program instructions include machine language codes, such as ones generated by a compiler, and high-level language codes executable by a computer using an interpreter, etc.

Although the embodiments of the present application have been described with reference to the limited embodiments and drawings, the technical idea or embodiments disclosed in the present specification are not limited to the above-described embodiments, and it will be understood by those skilled in the art that various modifications and variations may be made from the description. Therefore, the scope of the present application is defined not by the description above but by the following claims, and all their equivalents will fall within the scope and spirit of the present disclosure.

MODE FOR INVENTION

As described above, related matters have been described in Best Mode.

The invention claimed is:

1. A method of acquiring a facial image of a subject to analyze a degree of ocular proptosis, the method comprising:
acquiring a front image of the subject's face while guidance is given to satisfy a first photographing condition, wherein the first photographing condition includes a condition in which the subject's both eyes are placed at predetermined areas in a first captured image;
generating panorama guidance on the basis of position information of a first point and a second point extracted from the front image, wherein the panorama guidance is generated in a horizontal direction with respect to a front of the face, and the first point and the second point are spaced apart from each other in a vertical direction with respect to the front of the face;
providing guidance on movement of a photographing device to acquire a preview image corresponding to the panorama guidance, which comprises monitoring whether a vertical separation distance between the first point and the second point extracted from the preview image is within a predetermined error range with respect to an initial separation distance; and
acquiring a side image of the subject's face while guidance is given to satisfy a second photographing condition, wherein the second photographing condition includes a condition in which a vertical separation distance between the first point and the second point extracted from a second captured image is within the predetermined error range with respect to an initial separation distance, wherein in order for the acquired images to be used in calculating the degree of ocular proptosis, the first captured image includes iris areas of the subject and the second captured image includes an outer canthus and a cornea of one of the subject's eyes.

2. The method of claim 1, wherein the first photographing condition includes a condition in which a left-right rotation angle of the subject's face does not exceed a predetermined first reference value.

3. The method of claim 2, wherein the first photographing condition includes a condition in which a level of smiling of the subject based on facial expression information of the subject does not exceed a predetermined second reference value.

4. The method of claim 3, wherein the first photographing condition includes a condition in which an up-down rotation angle of the subject's face does not exceed a predetermined third reference value.

5. The method of claim 4, wherein the first photographing condition includes a condition in which ambient brightness does not exceed a fourth reference value.

6. The method of claim 1, wherein the second photographing condition includes a condition in which the subject's ear is placed at a predetermined area in the second captured image.

7. The method of claim 1, wherein the first point is a point at a tip of a nose, and the second point is a point at a tip of a chin in an outline of the face.

8. The method of claim 1, wherein the providing the guidance on the movement of the photographing device to acquire the preview image corresponding to the panorama guidance comprises:
acquiring the preview image according to a predetermined frame rate,
determining whether the vertical separation distance between the first point and the second point extracted from the acquired preview image is within the predetermined error range with respect to the initial separation distance, and
outputting the guidance for adjusting a distance between the photographing device and the face when it is determined that the vertical separation distance is out of the predetermined error range with respect to the initial separation distance.

9. The method of claim 8, wherein the outputting the guidance for adjusting the distance between the photographing device and the face comprises:
outputting the guidance for moving the photographing device away from the face when it is determined that the vertical separation distance between the first point and the second point extracted from the acquired preview image is longer than the initial separation distance by more than the predetermined error range, and
outputting the guidance for moving the photographing device close to the face when it is determined that the vertical separation distance between the first point and the second point extracted from the acquired preview image is shorter than the initial separation distance by more than the predetermined error range.

10. The method of claim 8, wherein the providing the guidance on the movement of the photographing device to acquire the preview image corresponding to the panorama guidance comprises:
determining whether a position of the first point extracted from the acquired preview image is moved by more than a fifth reference value from a position of the first point extracted from the front image, and
outputting the guidance for moving the photographing device upward or downward with respect to the face when it is determined that the position of the first point extracted from the acquired preview image is moved by more than the fifth reference value from the position of the first point extracted from the front image.

11. The method of claim 10, wherein the providing the guidance on the movement of the photographing device to acquire the preview image corresponding to the panorama guidance comprises:
determining whether a position of the second point extracted from the acquired preview image is moved by more than a sixth reference value from a position of the second point extracted from the front image, and
outputting the guidance for moving the photographing device upward or downward with respect to the face when it is determined that the position of the second point extracted from the acquired preview image is moved by more than the sixth reference value from the position of the second point extracted from the front image.

12. The method of claim 1, wherein the providing the guidance on the movement of the photographing device to acquire the preview image corresponding to the panorama guidance comprises:
acquiring a third captured image which is at least part of the preview image, and
storing a panoramic image in which the first captured image, the second captured image, and the third captured image are edited into.

13. The method of claim 1, wherein the method comprises:
storing video images which is continuously acquired from a time point at which the first captured image is acquired to a time point at which the second captured image is acquired.

14. The method of claim 1, wherein the second photographing condition includes a condition in which one of the subject's eyes is not detected in the second captured image.

15. An analysis method for the images acquired by performing the method of claim 1, the analysis method comprising:
acquiring a diameter value of the iris areas detected in the first captured image;
acquiring a distance value between the outer canthus and the cornea furthest from the outer canthus detected in the second captured image;
acquiring a ratio of the distance value to the diameter value; and
acquiring the degree of ocular proptosis by applying the acquired ratio to a characteristic value of the iris areas.

16. A non-transitory computer-readable medium storing one or more instructions, wherein when the one or more instructions is executed by one or more processors of a computing device, the one or more instructions cause the computing device to perform the method of claim 1.

17. A photographing device for acquiring a facial image of a subject to analyze a degree of ocular proptosis, the photographing device comprising:

a communication part;

a storage part configured to store one or more instructions therein; and a controller configured to execute the one or more instructions stored in the storage part, wherein the controller is configured to, by executing the one or more instructions, acquire a front image of the subject's face while guidance is given to satisfy a first photographing condition, generate panorama guidance on the basis of position information of a first point and a second point extracted from the front image, provide guidance on movement of the photographing device to acquire a preview image corresponding to the panorama guidance, and acquire a side image of the subject's face while guidance is given to satisfy a second photographing condition, and wherein the first photographing condition includes a condition in which the subject's both eyes are placed at predetermined areas in a first captured image, the panorama guidance is generated in a horizontal direction with respect to a front of the face, and the first point and the second point are spaced apart from each other in a vertical direction with respect to the front of the face, and the second photographing condition includes a condition in which a vertical separation distance between the first point and the second point extracted from a second captured image is within a predetermined error range with respect to an initial separation distance.

* * * * *